United States Patent [19]
Hiyoshi et al.

[11] Patent Number: 5,824,862
[45] Date of Patent: Oct. 20, 1998

[54] DNA ENCODING ATP-DEPENDENT FRUCTOSE 6-PHOSPHATE 1-PHOSPHOTRANSFERASE ORIGINATING FROM PLANT, RECOMBINANT VECTOR CONTAINING THE SAME AND METHOD FOR CHANGING SUGAR CONTENT IN PLANT CELLS UNDER LOW TEMPERATURE

[75] Inventors: Toru Hiyoshi; Toshiki Mine, both of Iwata-gun; Keisuke Kasaoka, Tokyo, all of Japan; Robert Huw Tyson; Anthony Miles John Page, both of Babraham, United Kingdom

[73] Assignee: Japan Tobacco Inc., Tokyo, Japan

[21] Appl. No.: 416,870

[22] PCT Filed: Aug. 16, 1994

[86] PCT No.: PCT/JP94/01352

§ 371 Date: Jun. 9, 1995

§ 102(e) Date: Jun. 9, 1995

[87] PCT Pub. No.: WO95/05457

PCT Pub. Date: Feb. 23, 1995

[30] Foreign Application Priority Data

Aug. 19, 1993 [JP] Japan .................................. 5-226454

[51] Int. Cl.$^6$ .............................. A01H 5/00; C12N 15/29; C12N 15/54; C12N 15/82
[52] U.S. Cl. ................................ 800/205; 800/DIG. 42; 435/69.1; 435/101; 435/172.3; 435/194; 435/252.3; 435/254.2; 435/320.1; 435/325; 435/366; 435/419; 536/23.2; 536/23.6; 426/438
[58] Field of Search .................................. 536/23.2, 23.6; 435/69.1, 70.1, 101, 172.3, 194, 320.1, 252.3, 254.2, 325, 366, 419; 800/205, DIG. 42; 426/438

[56] References Cited

FOREIGN PATENT DOCUMENTS 438904 7/1991 European Pat. Off. .
598493 5/1994 European Pat. Off. .

OTHER PUBLICATIONS

"Nucleic Acid Research" 17. 8385 (1989) Wen–jun et al.
Analytical Biochemistry 84, pp. 462–472 (1978) Tabita et al.
"Agricultural and Food Chemistry" vol. 7, No. 4, Apr. 1959—pp. 274–277 Shallen–berger et al.
"Biochemical Society Transactions" vol. 17—pp. 760–761 Kruger, N.
W.G. Burton "The Potato" 3rd edition, pp. 404–411, Longman Scientific & Technical: NY.
Dixon et al "Carbohydrate Metabolism During Cold–Induced Sweetening of Potato Tubers"—Dec. 1979.
Planta (1990) 180—pp. 613–616 Hammond et al.
"Archives of Biochemistry & Biophysics" vol. 267, #2, pp. 690–700, Dec. 1988 Kruger et al.
"Biotechnique" vol. 5, No. 4, (1987)—pp. 376–378 Bullock et al.
"Nature" vol. 279, pp. 500–504—Jun. 7, 1979 Evans et al.
"Plants & Temperature" No. 42, pp. 377–393, Long et al., eds., Cambridge U. Press: Cambridge UK ap Rees et al.
"Gene" 78 (1989) pp. 309–321 Heinisch et al.
"Planta" 194 (1994) pp. 95–101 Burrell et al.
P. M. Harris—"Potato Crop" Chapter 13, pp. 504–544, Chapman & Hall: London.
"Phytochemistry" vol. 14, pp. 613–617 (1975) Pollock et al.
"Phytochemistry" vol. 20, No. 5, pp. 969–172, (1981) Dixon et al.
"Nature" vol. 321—May 22, 1986—pp. 446–449 Baulcombe et al.
"The EMBO Journal" vol. 12, No. 2, pp. 379–386 (1993) Longstaff et al.
Thorens, Proc. Natl. Acad. Sci. USA, vol. 89, pp. 8641–8645 (Sep. 1992).
Cashdollar et al, Proc. Natl. Acd. Sci. USA, vol. 82, pp. 24–28 (Jan. 1985).
Llanos et al, Journal of Bacteriology, vol. 175, No. 9, pp. 2541–2551 (May 1993).
Hellinga et al, Eur. J. Biochem., 149, pp. 363–373 (1985).
Heinisch et al, Molecular Microbiology, 8(3), pp. 559–570 (1993).
French et al, Gene, vol. 54, pp. 65–71 (1987).
Carlisle et al. 1990. J. Biol. Chem. 265(30):18366–18371.
Blakeley et al. 1992. Plant Physiol. 99(3):1245–1250.

*Primary Examiner*—David T. Fox
*Attorney, Agent, or Firm*—Birch, Stewart, Kolasch & Birch, LLP

[57] ABSTRACT

A DNA encoding cold stable PFK, a recombinant vector which can express a cold stable PFK in a host cell, and a method for changing sugar content in plant cells under low temperature using the recombinant vector are disclosed. The present invention provides a DNA encoding ATP dependent fructose 6-phosphate 1-phosphotransferase originating from a plant, as well as a recombinant vector comprising the DNA and a plant transformed with the DNA.

37 Claims, 5 Drawing Sheets

CBB STAINING

WESTERN BLOT ANALYSIS
(ANTI-POTATO PFK-c ANTIBODY)

LANE 1: MOLECULAR WEIGHT MARKER
LANE 2 AND 3: CRUDE EXTRACT SOLUTION OF E.COLI XL1-BLUE
LANE 4: AFTER PURIFICATION BY CIBACRON BLUE AGAROSE (FLOW THROUGH)
LANE 5: AFTER PURIFICATION BY REACTIVE RED 120- AGAROSE (ELUTED BY KCl)
LANE 6: AFTER PURIFICATION BY MONO Q
LANE 7: PFK PURIFIED FROM POTATO TUBERS

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1978 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 133..1587

( x i ) SEQUENCE DESCRIPTION: SEQ ID NO:1:

```
CTCTTTTCTT  GGGTTGACTC  AAATTTAACA  TATATATGTA  TTTTTTTGTT  TTTGTGATTC           60

TGTTTTCAGA  TACCCTTTTG  AATTTCCATT  GAGAAAGTTG  GAATCTTTTT  TGTTTTTATA          120

TATTTGGGGA AG  ATG GGT ACT GAG AGT AAT TAC CAG ATG AAG GTG GTG                 168
               Met Gly Thr Glu Ser Asn Tyr Gln Met Lys Val Val
                1               5                  10

AAA GGA GAT TAT GGC TAT GTT CTT GAA GAT GTT CCT CAT TTG ACT GAT                216
Lys Gly Asp Tyr Gly Tyr Val Leu Glu Asp Val Pro His Leu Thr Asp
             15                  20                  25

TAT ATC CCT GAT CTT CCT ACT TAT GAC AAT CCA TTG CGG TCC AAT CCT                264
Tyr Ile Pro Asp Leu Pro Thr Tyr Asp Asn Pro Leu Arg Ser Asn Pro
         30                  35                  40

GCA TAT TCA GTT GTG AAG CAG TAC TTT GTT GAC ATG GAT GAT ACT GTC                312
Ala Tyr Ser Val Val Lys Gln Tyr Phe Val Asp Met Asp Asp Thr Val
 45                  50                  55                  60

CCC CAA AAG GTT GTT GTT CAC AAG GAC AGT CCC AGA GGG GTG CAT TTC                360
Pro Gln Lys Val Val Val His Lys Asp Ser Pro Arg Gly Val His Phe
                 65                  70                  75

CGG CGT GCT GGT CCA CGT CAG AAG GTG TAT TTC AGT TCG GAT GAT GTT                408
Arg Arg Ala Gly Pro Arg Gln Lys Val Tyr Phe Ser Ser Asp Asp Val
             80                  85                  90
```

| | | | | | | | | | | | | | | | | |
|---|---|---|---|---|---|---|---|---|---|---|---|---|---|---|---|---|
| CGT | GCT | TGT | ATT | GTA | ACT | TGT | GGT | GGT | TTG | TGC | CCT | GGG | CTA | AAC | ACA | 456 |
| Arg | Ala | Cys | Ile | Val | Thr | Cys | Gly | Gly | Leu | Cys | Pro | Gly | Leu | Asn | Thr | |
| | | 95 | | | | | 100 | | | | | 105 | | | | |
| GTG | ATC | AGA | GAG | ATT | GTA | CAT | AGC | CTC | GAT | TAT | ATG | TAT | GGA | GTC | AAC | 504 |
| Val | Ile | Arg | Glu | Ile | Val | His | Ser | Leu | Asp | Tyr | Met | Tyr | Gly | Val | Asn | |
| | 110 | | | | | 115 | | | | | 120 | | | | | |
| AAA | GTC | TTT | GGT | ATC | GAT | GGA | GGC | TAC | AGG | GGT | TTC | TAT | TCC | AAG | AAT | 552 |
| Lys | Val | Phe | Gly | Ile | Asp | Gly | Gly | Tyr | Arg | Gly | Phe | Tyr | Ser | Lys | Asn | |
| 125 | | | | | 130 | | | | | 135 | | | | | 140 | |
| ATC | ATC | AAT | TTG | ACA | CCA | AAG | ACT | GTT | AAT | GAC | ATT | CAT | AAA | CGT | GGT | 600 |
| Ile | Ile | Asn | Leu | Thr | Pro | Lys | Thr | Val | Asn | Asp | Ile | His | Lys | Arg | Gly | |
| | | | | 145 | | | | | 150 | | | | | 155 | | |
| GGT | ACA | ATT | CTT | GGA | TCA | TCA | CGA | GGA | GGC | CAT | GAT | ACC | ACA | AAG | ATT | 648 |
| Gly | Thr | Ile | Leu | Gly | Ser | Ser | Arg | Gly | Gly | His | Asp | Thr | Thr | Lys | Ile | |
| | | | 160 | | | | | 165 | | | | | 170 | | | |
| GTT | GAC | AGC | ATA | CAG | GAC | CGT | GAA | ATT | AAT | CAG | GTA | TAT | ATA | ATC | GGT | 696 |
| Val | Asp | Ser | Ile | Gln | Asp | Arg | Glu | Ile | Asn | Gln | Val | Tyr | Ile | Ile | Gly | |
| | | 175 | | | | | 180 | | | | | 185 | | | | |
| GGT | GAT | GGA | ACT | CAG | AAA | GGA | GCA | GCT | GTA | ATA | TAT | GAG | GAA | ATC | AGG | 744 |
| Gly | Asp | Gly | Thr | Gln | Lys | Gly | Ala | Ala | Val | Ile | Tyr | Glu | Glu | Ile | Arg | |
| | | 190 | | | | | 195 | | | | | 200 | | | | |
| CGG | CGT | GGT | CTC | AAA | GTA | ATT | GTT | GCT | GGG | ATC | CCA | AAG | ACA | ATT | GAT | 792 |
| Arg | Arg | Gly | Leu | Lys | Val | Ile | Val | Ala | Gly | Ile | Pro | Lys | Thr | Ile | Asp | |
| 205 | | | | | 210 | | | | | 215 | | | | | 220 | |
| AAT | GAT | ATC | CCT | GTT | ATC | GAC | AAG | TCA | TTT | GGT | TTT | GAT | ACT | GCT | GTA | 840 |
| Asn | Asp | Ile | Pro | Val | Ile | Asp | Lys | Ser | Phe | Gly | Phe | Asp | Thr | Ala | Val | |
| | | | | 225 | | | | | 230 | | | | | 235 | | |
| GAG | GAG | GCT | CAA | CGT | GCC | ATA | AAT | GCA | GCT | CAT | GTT | GAA | GCT | GAA | AGT | 888 |
| Glu | Glu | Ala | Gln | Arg | Ala | Ile | Asn | Ala | Ala | His | Val | Glu | Ala | Glu | Ser | |
| | | | 240 | | | | | 245 | | | | | 250 | | | |
| GCT | GAA | AAT | GGT | ATT | GGT | GTG | GTG | AAG | CTA | ATG | GGA | CGC | TAT | AGT | GGA | 936 |
| Ala | Glu | Asn | Gly | Ile | Gly | Val | Val | Lys | Leu | Met | Gly | Arg | Tyr | Ser | Gly | |
| | | 255 | | | | | 260 | | | | | 265 | | | | |
| TTC | ATC | GCA | ATG | TAT | GCC | ACT | TTG | GCG | AGC | AGA | GAT | GTT | GAT | CTC | TGT | 984 |
| Phe | Ile | Ala | Met | Tyr | Ala | Thr | Leu | Ala | Ser | Arg | Asp | Val | Asp | Leu | Cys | |
| 270 | | | | | 275 | | | | | 280 | | | | | | |
| TTA | ATT | CCA | GAG | TCA | CCC | TTT | TAT | CTT | GAA | GGA | GAT | GGT | GGA | CTC | TTT | 1032 |
| Leu | Ile | Pro | Glu | Ser | Pro | Phe | Tyr | Leu | Glu | Gly | Asp | Gly | Gly | Leu | Phe | |
| 285 | | | | | 290 | | | | | 295 | | | | | 300 | |
| GAA | TAC | ATT | GAA | AAA | AGG | CTC | AAA | GAA | AAT | GGG | CAC | ATG | GTT | ATT | GTG | 1080 |
| Glu | Tyr | Ile | Glu | Lys | Arg | Leu | Lys | Glu | Asn | Gly | His | Met | Val | Ile | Val | |
| | | | | 305 | | | | | 310 | | | | | 315 | | |
| ATA | GCC | GAA | GGA | GCA | GGG | CAA | GAA | CTT | CTT | GCA | GAA | GAG | AAT | GCG | CAT | 1128 |
| Ile | Ala | Glu | Gly | Ala | Gly | Gln | Glu | Leu | Leu | Ala | Glu | Glu | Asn | Ala | His | |
| | | | 320 | | | | | 325 | | | | | 330 | | | |
| GCC | AAA | AAC | GAA | CAA | GAT | GCT | TCG | GGG | AAC | AAG | CTT | CTC | CAG | GAT | GTT | 1176 |
| Ala | Lys | Asn | Glu | Gln | Asp | Ala | Ser | Gly | Asn | Lys | Leu | Leu | Gln | Asp | Val | |
| | | 335 | | | | | 340 | | | | | 345 | | | | |
| GGT | TTG | TGG | ATT | TCC | CAA | AAA | ATC | AGG | GAT | CAT | TTT | GCT | ACA | AAA | ACT | 1224 |
| Gly | Leu | Trp | Ile | Ser | Gln | Lys | Ile | Arg | Asp | His | Phe | Ala | Thr | Lys | Thr | |
| | 350 | | | | | 355 | | | | | 360 | | | | | |
| AAG | ATG | CCC | ATT | ACT | CTT | AAG | TAT | ATA | GAT | CCG | ACT | TAC | ATG | ATT | CGT | 1272 |
| Lys | Met | Pro | Ile | Thr | Leu | Lys | Tyr | Ile | Asp | Pro | Thr | Tyr | Met | Ile | Arg | |
| 365 | | | | | 370 | | | | | 375 | | | | | 380 | |
| GCT | GTT | CCA | AGT | AAT | GCC | TCT | GAT | AAT | GTA | TAT | TGC | ACT | CTT | CTT | GCT | 1320 |
| Ala | Val | Pro | Ser | Asn | Ala | Ser | Asp | Asn | Val | Tyr | Cys | Thr | Leu | Leu | Ala | |
| | | | | 385 | | | | | 390 | | | | | 395 | | |
| CAA | AGT | TGT | GTT | CAT | GGA | GCA | ATG | GCA | GGC | TAC | ACA | GGT | TTC | ACC | TCA | 1368 |
| Gln | Ser | Cys | Val | His | Gly | Ala | Met | Ala | Gly | Tyr | Thr | Gly | Phe | Thr | Ser | |
| | | | | 400 | | | | | 405 | | | | | 410 | | |

-continued

| | | | | | | | | | | | | | | | | |
|---|---|---|---|---|---|---|---|---|---|---|---|---|---|---|---|---|
| GGA | CTT | GTC | AAT | GGT | CGC | CAG | ACT | TAT | ATA | CCA | TTC | AAT | CGT | ATT | ACC | 1416 |
| Gly | Leu | Val | Asn | Gly | Arg | Gln | Thr | Tyr | Ile | Pro | Phe | Asn | Arg | Ile | Thr | |
| | | 415 | | | | | 420 | | | | | 425 | | | | |
| GAG | AAA | CAA | AAT | ATG | GTG | GTT | ATA | ACT | GAC | AGG | ATG | TGG | GCA | CGT | CTT | 1464 |
| Glu | Lys | Gln | Asn | Met | Val | Val | Ile | Thr | Asp | Arg | Met | Trp | Ala | Arg | Leu | |
| 430 | | | | | 435 | | | | | 440 | | | | | | |
| CTT | TCG | TCA | ACC | AAT | CAG | CCA | AGC | TTC | TTG | CGC | GTG | AAA | GAC | ATT | GAA | 1512 |
| Leu | Ser | Ser | Thr | Asn | Gln | Pro | Ser | Phe | Leu | Arg | Val | Lys | Asp | Ile | Glu | |
| 445 | | | | 450 | | | | | 455 | | | | | 460 | | |
| GAG | ATT | AAA | AAG | GAG | GAG | CAG | CCG | CAA | ACT | CAA | CTG | TTG | GAT | GGG | GAT | 1560 |
| Glu | Ile | Lys | Lys | Glu | Glu | Gln | Pro | Gln | Thr | Gln | Leu | Leu | Asp | Gly | Asp | |
| | | | | 465 | | | | | 470 | | | | | 475 | | |
| AAC | AAT | GTA | CAT | GAG | AAC | TCA | GGT | CAC | TGATACAGTA | ATTACGAACT | | | | | | 1607 |
| Asn | Asn | Val | His | Glu | Asn | Ser | Gly | His | | | | | | | | |
| | | | 480 | | | | | 485 | | | | | | | | |

| | | | | | |
|---|---|---|---|---|---|
| TGGCGTGACA | CACTGAAGTA | ACTCTGTTGT | AATCATTTGC | CTGTGCAGTG | GTTCTCTTGT | 1667 |
| TGTCTTTGAA | GCTTTTGCTG | CTTACCATTG | TGCCTTATAA | AAACAGTCCT | AGGAACTTAT | 1727 |
| TTGTTGAAGG | TTTTGGGATC | TTCTGCATCA | GATGTTGGCA | GTAGTAACAG | ATATATTTCT | 1787 |
| GCCTAATTCA | TCTAGAGTCC | TAATTTCTTG | AAGTGAAATT | AGACATCTTT | TTATAAAATA | 1847 |
| TTTTGTAATA | AATTTAAATA | GTGAGAACAT | TTGCTATGCA | CATAAATGAT | GAACTCTGTG | 1907 |
| TGGCTGGATG | GTCTTTTGAG | ATCTAAAATA | GTCCAAGATT | TTGGCAGAAA | TCAGAAGTAG | 1967 |
| AGGCAGACTT | T | | | | | 1978 |

( 2 ) INFORMATION FOR SEQ ID NO:2:

( i ) SEQUENCE CHARACTERISTICS:
        ( A ) LENGTH: 485 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Gly | Thr | Glu | Ser | Asn | Tyr | Gln | Met | Lys | Val | Val | Lys | Gly | Asp | Tyr |
| 1 | | | | 5 | | | | | 10 | | | | | 15 | |
| Gly | Tyr | Val | Leu | Glu | Asp | Val | Pro | His | Leu | Thr | Asp | Tyr | Ile | Pro | Asp |
| | | | 20 | | | | | 25 | | | | | 30 | | |
| Leu | Pro | Thr | Tyr | Asp | Asn | Pro | Leu | Arg | Ser | Asn | Pro | Ala | Tyr | Ser | Val |
| | | | 35 | | | | 40 | | | | | 45 | | | |
| Val | Lys | Gln | Tyr | Phe | Val | Asp | Met | Asp | Asp | Thr | Val | Pro | Gln | Lys | Val |
| | | 50 | | | | | 55 | | | | | 60 | | | |
| Val | Val | His | Lys | Asp | Ser | Pro | Arg | Gly | Val | His | Phe | Arg | Arg | Ala | Gly |
| 65 | | | | | 70 | | | | | 75 | | | | | 80 |
| Pro | Arg | Gln | Lys | Val | Tyr | Phe | Ser | Ser | Asp | Asp | Val | Arg | Ala | Cys | Ile |
| | | | | 85 | | | | | 90 | | | | | 95 | |
| Val | Thr | Cys | Gly | Gly | Leu | Cys | Pro | Gly | Leu | Asn | Thr | Val | Ile | Arg | Glu |
| | | | | 100 | | | | | 105 | | | | | 110 | |
| Ile | Val | His | Ser | Leu | Asp | Tyr | Met | Tyr | Gly | Val | Asn | Lys | Val | Phe | Gly |
| | | | 115 | | | | | 120 | | | | | 125 | | |
| Ile | Asp | Gly | Gly | Tyr | Arg | Gly | Phe | Tyr | Ser | Lys | Asn | Ile | Ile | Asn | Leu |
| | | | 130 | | | | | 135 | | | | | 140 | | |
| Thr | Pro | Lys | Thr | Val | Asn | Asp | Ile | His | Lys | Arg | Gly | Gly | Thr | Ile | Leu |
| 145 | | | | | 150 | | | | | 155 | | | | | 160 |
| Gly | Ser | Ser | Arg | Gly | Gly | His | Asp | Thr | Thr | Lys | Ile | Val | Asp | Ser | Ile |
| | | | | 165 | | | | | 170 | | | | | 175 | |

-continued

```
Gln  Asp  Arg  Glu  Ile  Asn  Gln  Val  Tyr  Ile  Ile  Gly  Gly  Asp  Gly  Thr
               180                      185                     190
Gln  Lys  Gly  Ala  Ala  Val  Ile  Tyr  Glu  Glu  Ile  Arg  Arg  Gly  Leu
          195                      200                     205
Lys  Val  Ile  Val  Ala  Gly  Ile  Pro  Lys  Thr  Ile  Asn  Asp  Ile  Pro
     210                      215                     220
Val  Ile  Asp  Lys  Ser  Phe  Gly  Phe  Asp  Thr  Ala  Val  Glu  Glu  Ala  Gln
225                      230                 235                          240
Arg  Ala  Ile  Asn  Ala  Ala  His  Val  Glu  Ala  Glu  Ser  Ala  Glu  Asn  Gly
               245                      250                     255
Ile  Gly  Val  Val  Lys  Leu  Met  Gly  Arg  Tyr  Ser  Gly  Phe  Ile  Ala  Met
               260                      265                     270
Tyr  Ala  Thr  Leu  Ala  Ser  Arg  Asp  Val  Asp  Leu  Cys  Leu  Ile  Pro  Glu
          275                      280                     285
Ser  Pro  Phe  Tyr  Leu  Glu  Gly  Asp  Gly  Gly  Leu  Phe  Glu  Tyr  Ile  Glu
     290                      295                     300
Lys  Arg  Leu  Lys  Glu  Asn  Gly  His  Met  Val  Ile  Val  Ile  Ala  Glu  Gly
305                      310                 315                          320
Ala  Gly  Gln  Glu  Leu  Ala  Glu  Glu  Asn  Ala  His  Ala  Lys  Asn  Glu
                    325                      330                     335
Gln  Asp  Ala  Ser  Gly  Asn  Lys  Leu  Leu  Gln  Asp  Val  Gly  Leu  Trp  Ile
               340                      345                     350
Ser  Gln  Lys  Ile  Arg  Asp  His  Phe  Ala  Thr  Lys  Thr  Lys  Met  Pro  Ile
          355                      360                     365
Thr  Leu  Lys  Tyr  Ile  Asp  Pro  Thr  Tyr  Met  Ile  Arg  Ala  Val  Pro  Ser
     370                      375                     380
Asn  Ala  Ser  Asp  Asn  Val  Tyr  Cys  Thr  Leu  Leu  Ala  Gln  Ser  Cys  Val
385                      390                 395                          400
His  Gly  Ala  Met  Ala  Gly  Tyr  Thr  Gly  Phe  Thr  Ser  Gly  Leu  Val  Asn
                    405                      410                     415
Gly  Arg  Gln  Thr  Tyr  Ile  Pro  Phe  Asn  Arg  Ile  Thr  Glu  Lys  Gln  Asn
               420                      425                     430
Met  Val  Val  Ile  Thr  Asp  Arg  Met  Trp  Ala  Arg  Leu  Leu  Ser  Ser  Thr
          435                      440                     445
Asn  Gln  Pro  Ser  Phe  Leu  Arg  Val  Lys  Asp  Ile  Glu  Glu  Ile  Lys  Lys
     450                      455                     460
Glu  Glu  Gln  Pro  Gln  Thr  Gln  Leu  Leu  Asp  Gly  Asp  Asn  Asn  Val  His
465                      470                 475                          480
Glu  Asn  Ser  Gly  His
               485
```

( 2 ) INFORMATION FOR SEQ ID NO:3:

( i ) SEQUENCE CHARACTERISTICS:
        ( A ) LENGTH: 1778 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 19..1467

( x i ) SEQUENCE DESCRIPTION: SEQ ID NO:3:

```
GTTAACAAGG  GGGAAGTT  ATG  GAT  AAT  AAC  ATC  AGT  TGT  GAG  ATG  AAA  GTT        51
                      Met  Asp  Asn  Asn  Ile  Ser  Cys  Glu  Met  Lys  Val
                       1                 5                        10
```

| | | | | | | | | | | | | | | | | |
|---|---|---|---|---|---|---|---|---|---|---|---|---|---|---|---|---|
| GAA | ACA | GGG | GAT | GCA | GGC | TAT | GTG | CTT | GAA | GAT | GTG | CCT | CAC | ATA | ACT | 99 |
| Glu | Thr | Gly | Asp | Ala | Gly | Tyr | Val | Leu | Glu | Asp | Val | Pro | His | Ile | Thr | |
| | | | 15 | | | | 20 | | | | | 25 | | | | |
| GAT | TAC | ATC | CCT | AAT | CTC | CCT | ACC | TAT | CCT | AAT | CCA | TTG | CGT | TCT | AAT | 147 |
| Asp | Tyr | Ile | Pro | Asn | Leu | Pro | Thr | Tyr | Pro | Asn | Pro | Leu | Arg | Ser | Asn | |
| | | 30 | | | | | 35 | | | | | 40 | | | | |
| CCT | GCA | TAT | TCG | GTT | GTG | AAG | CAG | TAC | TTT | GTT | GAT | GCG | GAT | GAT | ACC | 195 |
| Pro | Ala | Tyr | Ser | Val | Val | Lys | Gln | Tyr | Phe | Val | Asp | Ala | Asp | Asp | Thr | |
| | | 45 | | | | | 50 | | | | | 55 | | | | |
| GTG | CCT | CAA | AAG | GTT | GTT | GTA | CAC | AAG | GAC | GGT | CCA | AGA | GGA | ATA | CAC | 243 |
| Val | Pro | Gln | Lys | Val | Val | Val | His | Lys | Asp | Gly | Pro | Arg | Gly | Ile | His | |
| 60 | | | | | 65 | | | | | 70 | | | | | 75 | |
| TTT | CGA | CGT | GCT | GGT | CCT | CGT | CAA | AGG | GTT | TAT | TTT | GCA | CCA | GAT | GAA | 291 |
| Phe | Arg | Arg | Ala | Gly | Pro | Arg | Gln | Arg | Val | Tyr | Phe | Ala | Pro | Asp | Glu | |
| | | | | 80 | | | | | 85 | | | | | 90 | | |
| GTG | CAT | GCT | GCT | ATA | GTA | ACA | TGT | GGT | GGT | TTA | TGT | CCT | GGG | CTA | AAC | 339 |
| Val | His | Ala | Ala | Ile | Val | Thr | Cys | Gly | Gly | Leu | Cys | Pro | Gly | Leu | Asn | |
| | | | 95 | | | | | 100 | | | | | 105 | | | |
| ACA | GTG | ATC | AGG | GAA | ATT | GTT | TGC | GCA | CTT | TAT | CAC | ATG | TAT | GGT | GTC | 387 |
| Thr | Val | Ile | Arg | Glu | Ile | Val | Cys | Ala | Leu | Tyr | His | Met | Tyr | Gly | Val | |
| | | 110 | | | | | 115 | | | | | 120 | | | | |
| ACC | AAA | GTT | CTT | GGG | ATT | GAT | GGA | GGG | TAC | AGA | GGT | TTT | TAC | TCA | AAA | 435 |
| Thr | Lys | Val | Leu | Gly | Ile | Asp | Gly | Gly | Tyr | Arg | Gly | Phe | Tyr | Ser | Lys | |
| | 125 | | | | | 130 | | | | | 135 | | | | | |
| AAC | ACC | ATC | ACT | TTG | ACT | CCA | AAG | GTT | GTG | AAT | GAC | ATC | CAT | AAA | CGT | 483 |
| Asn | Thr | Ile | Thr | Leu | Thr | Pro | Lys | Val | Val | Asn | Asp | Ile | His | Lys | Arg | |
| 140 | | | | | 145 | | | | | 150 | | | | | 155 | |
| GGT | GGT | ACA | ATT | ATT | GGC | ACC | TCT | CGT | GGG | GGC | CAT | GAT | AAA | CCA | AAG | 531 |
| Gly | Gly | Thr | Ile | Ile | Gly | Thr | Ser | Arg | Gly | Gly | His | Asp | Lys | Pro | Lys | |
| | | | | 160 | | | | | 165 | | | | | 170 | | |
| ATA | GTT | GAC | AGT | ATT | CAG | GAT | CGT | GGT | ATC | AAT | CAG | GTT | TAT | ATA | ATT | 579 |
| Ile | Val | Asp | Ser | Ile | Gln | Asp | Arg | Gly | Ile | Asn | Gln | Val | Tyr | Ile | Ile | |
| | | | 175 | | | | | 180 | | | | | 185 | | | |
| GGA | GGA | GAC | GGT | ACT | CAA | AAG | GGA | GCA | GCT | GTT | ATT | TAT | CAG | GAA | GTG | 627 |
| Gly | Gly | Asp | Gly | Thr | Gln | Lys | Gly | Ala | Ala | Val | Ile | Tyr | Gln | Glu | Val | |
| | | 190 | | | | | 195 | | | | | 200 | | | | |
| AGA | AGG | CGT | GGG | CTT | AAA | GCT | GTA | GTG | GCT | GGG | ATT | CCT | AAG | ACA | ATT | 675 |
| Arg | Arg | Arg | Gly | Leu | Lys | Ala | Val | Val | Ala | Gly | Ile | Pro | Lys | Thr | Ile | |
| | 205 | | | | | 210 | | | | | 215 | | | | | |
| GAT | AAT | GAC | ATT | CCG | GTC | ATT | GAT | AAG | TCT | TTT | GGT | TTT | GAC | ACG | GCT | 723 |
| Asp | Asn | Asp | Ile | Pro | Val | Ile | Asp | Lys | Ser | Phe | Gly | Phe | Asp | Thr | Ala | |
| 220 | | | | | 225 | | | | | 230 | | | | | 235 | |
| GTG | GAA | GAG | GCT | CAA | CGT | GCC | ATT | AAT | GCT | GCA | CAT | GTG | GAG | GCT | GAA | 771 |
| Val | Glu | Glu | Ala | Gln | Arg | Ala | Ile | Asn | Ala | Ala | His | Val | Glu | Ala | Glu | |
| | | | | 240 | | | | | 245 | | | | | 250 | | |
| AGT | GCT | GAG | AAT | GGC | ATA | GGG | GTG | GTC | AAA | CTT | ATG | GGA | CGC | TAT | AGT | 819 |
| Ser | Ala | Glu | Asn | Gly | Ile | Gly | Val | Val | Lys | Leu | Met | Gly | Arg | Tyr | Ser | |
| | | | 255 | | | | | 260 | | | | | 265 | | | |
| GGA | TTC | ATC | GCA | ATG | TAT | GCA | ACT | TTG | GCT | AGT | CGA | GAT | GTT | GAT | TTA | 867 |
| Gly | Phe | Ile | Ala | Met | Tyr | Ala | Thr | Leu | Ala | Ser | Arg | Asp | Val | Asp | Leu | |
| | | 270 | | | | | 275 | | | | | 280 | | | | |
| TGT | TTA | ATT | CCT | GAA | TCA | CCT | TTT | TAT | CTT | GAG | GGA | GAA | GGT | GGA | CTT | 915 |
| Cys | Leu | Ile | Pro | Glu | Ser | Pro | Phe | Tyr | Leu | Glu | Gly | Glu | Gly | Gly | Leu | |
| | 285 | | | | | 290 | | | | | 295 | | | | | |
| TTA | GAA | TAT | GTA | GAA | AAA | CGT | CTC | AAG | GAC | GAT | GGA | CAC | ATG | GTC | ATC | 963 |
| Leu | Glu | Tyr | Val | Glu | Lys | Arg | Leu | Lys | Asp | Asp | Gly | His | Met | Val | Ile | |
| 300 | | | | | 305 | | | | | 310 | | | | | 315 | |
| GTT | GTA | GCA | GAA | GGT | GCT | GGT | CAG | GAG | CTG | CTT | GCA | GCA | GAA | AAC | TTG | 1011 |
| Val | Val | Ala | Glu | Gly | Ala | Gly | Gln | Glu | Leu | Leu | Ala | Ala | Glu | Asn | Leu | |
| | | | | 320 | | | | | 325 | | | | | 330 | | |

```
AAA  ACT  TCA  ACC  GCA  AAA  GAT  GCT  TCT  GGA  AAT  AAA  CTA  CTT  CAC  GAT        1059
Lys  Thr  Ser  Thr  Ala  Lys  Asp  Ala  Ser  Gly  Asn  Lys  Leu  Leu  His  Asp
               335                           340                          345

GTC  GGA  TTG  TGG  ATT  TCT  GAT  AAG  ATT  AAG  GCT  CAC  TTT  GCT  AAA  ATT        1107
Val  Gly  Leu  Trp  Ile  Ser  Asp  Lys  Ile  Lys  Ala  His  Phe  Ala  Lys  Ile
          350                           355                      360

CCT  CCC  ATG  CCT  ATT  ACT  CTC  AAA  TAC  ATA  GAT  CCA  ACT  TAC  ATG  ATC        1155
Pro  Pro  Met  Pro  Ile  Thr  Leu  Lys  Tyr  Ile  Asp  Pro  Thr  Tyr  Met  Ile
     365                           370                      375

CGT  GCG  GTT  CCA  AGT  AAT  GCA  TCT  GAT  AAT  GTA  TAC  TGC  ACT  CTC  CTT        1203
Arg  Ala  Val  Pro  Ser  Asn  Ala  Ser  Asp  Asn  Val  Tyr  Cys  Thr  Leu  Leu
380                      385                      390                          395

GCT  CAA  AGT  TGT  GTT  CAT  GGA  GTG  ATG  GCG  GGC  TAC  ACC  GGC  TTC  ACA        1251
Ala  Gln  Ser  Cys  Val  His  Gly  Val  Met  Ala  Gly  Tyr  Thr  Gly  Phe  Thr
                         400                      405                      410

AGT  GGG  CTT  GTC  AAT  GGT  AGA  CAG  ACT  TAT  ATT  CCA  TTT  AAT  CGT  ATC        1299
Ser  Gly  Leu  Val  Asn  Gly  Arg  Gln  Thr  Tyr  Ile  Pro  Phe  Asn  Arg  Ile
                415                      420                      425

ACT  GAG  AAG  CAG  AAT  AAC  GTT  GTG  ATA  ACC  GAT  AGG  ATG  TGG  GCA  AGG        1347
Thr  Glu  Lys  Gln  Asn  Asn  Val  Val  Ile  Thr  Asp  Arg  Met  Trp  Ala  Arg
          430                      435                      440

CTT  CTG  TCA  TCC  ACC  AAC  CAA  CCA  AGC  TTT  TTG  CGA  CCC  CAA  GAC  GTT        1395
Leu  Leu  Ser  Ser  Thr  Asn  Gln  Pro  Ser  Phe  Leu  Arg  Pro  Gln  Asp  Val
     445                      450                      455

ATT  GAA  GTC  CAG  AAA  CAA  GAA  GAA  CCA  CCA  AGT  CAG  TTA  TTG  GAT  GGA        1443
Ile  Glu  Val  Gln  Lys  Gln  Glu  Glu  Pro  Pro  Ser  Gln  Leu  Leu  Asp  Gly
460                      465                      470                      475

GAC  AGC  AGC  AAG  CCA  AAT  GAC  ATC  TAAATCTATA  AATTAAGAAT  ATTCGCCATT           1497
Asp  Ser  Ser  Lys  Pro  Asn  Asp  Ile
                    480

TTAATGCACA  AAAATAATAG  CACTGCAAAT  TTGGTTTTGT  GGATGCAATT  CATCATGTTT              1557

TTGCAGAATT  TTCAAGATAA  AGTTGCTTAT  TCTTGACTGG  ATTGATCATG  GATTTAAGTC              1617

TCTTTGCAGG  AATGAATTTT  CCTCCAAAAA  AGAAACTGC   ATAAAACCTA  GTTTGTTGT               1677

GTTGGGATCA  AGCTATTGGT  AGTCAAGTTA  GAAAGTTTAA  GCTGCAGTTT  GTAATTGTTT              1737

GTGTTTGTTG  GGTTAAGTGG  CTTTGTTCAT  CAGAAAAAAA  A                                  1778
```

( 2 ) INFORMATION FOR SEQ ID NO:4:

( i ) SEQUENCE CHARACTERISTICS:
        ( A ) LENGTH: 483 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Asp  Asn  Asn  Ile  Ser  Cys  Glu  Met  Lys  Val  Glu  Thr  Gly  Asp  Ala
1                   5                   10                      15

Gly  Tyr  Val  Leu  Glu  Asp  Val  Pro  His  Ile  Thr  Asp  Tyr  Ile  Pro  Asn
          20                      25                      30

Leu  Pro  Thr  Tyr  Pro  Asn  Pro  Leu  Arg  Ser  Asn  Pro  Ala  Tyr  Ser  Val
               35                      40                      45

Val  Lys  Gln  Tyr  Phe  Val  Asp  Ala  Asp  Thr  Val  Pro  Gln  Lys  Val
     50                      55                      60

Val  Val  His  Lys  Asp  Gly  Pro  Arg  Gly  Ile  His  Phe  Arg  Arg  Ala  Gly
65                      70                      75                      80

Pro  Arg  Gln  Arg  Val  Tyr  Phe  Ala  Pro  Asp  Glu  Val  His  Ala  Ala  Ile
                    85                      90                      95
```

| | | | | | | | | | | | | | | |
|---|---|---|---|---|---|---|---|---|---|---|---|---|---|---|
|Val|Thr|Cys|Gly<br>100|Gly|Leu|Cys|Pro|Gly<br>105|Leu|Asn|Thr|Val|Ile<br>110|Arg|Glu|
|Ile|Val|Cys<br>115|Ala|Leu|Tyr|His|Met<br>120|Tyr|Gly|Val|Thr|Lys<br>125|Val|Leu|Gly|
|Ile|Asp<br>130|Gly|Gly|Tyr|Arg|Gly<br>135|Phe|Tyr|Ser|Lys|Asn<br>140|Thr|Ile|Thr|Leu|
|Thr<br>145|Pro|Lys|Val|Val|Asn<br>150|Asp|Ile|His|Lys|Arg<br>155|Gly|Gly|Thr|Ile|Ile<br>160|
|Gly|Thr|Ser|Arg|Gly<br>165|Gly|His|Asp|Lys|Pro<br>170|Lys|Ile|Val|Asp|Ser<br>175|Ile|
|Gln|Asp|Arg|Gly<br>180|Ile|Asn|Gln|Val|Tyr<br>185|Ile|Ile|Gly|Gly|Asp<br>190|Gly|Thr|
|Gln|Lys|Gly<br>195|Ala|Ala|Val|Ile|Tyr<br>200|Gln|Glu|Val|Arg|Arg<br>205|Arg|Gly|Leu|
|Lys|Ala<br>210|Val|Val|Ala|Gly|Ile<br>215|Pro|Lys|Thr|Ile|Asp<br>220|Asn|Asp|Ile|Pro|
|Val<br>225|Ile|Asp|Lys|Ser|Phe<br>230|Gly|Phe|Asp|Thr|Ala<br>235|Val|Glu|Glu|Ala|Gln<br>240|
|Arg|Ala|Ile|Asn|Ala<br>245|Ala|His|Val|Glu|Ala<br>250|Glu|Ser|Ala|Glu|Asn<br>255|Gly|
|Ile|Gly|Val|Val<br>260|Lys|Leu|Met|Gly|Arg<br>265|Tyr|Ser|Gly|Phe|Ile<br>270|Ala|Met|
|Tyr|Ala|Thr<br>275|Leu|Ala|Ser|Arg|Asp<br>280|Val|Asp|Leu|Cys|Leu<br>285|Ile|Pro|Glu|
|Ser|Pro<br>290|Phe|Tyr|Leu|Glu|Gly<br>295|Glu|Gly|Gly|Leu|Leu<br>300|Glu|Tyr|Val|Glu|
|Lys<br>305|Arg|Leu|Lys|Asp|Asp<br>310|Gly|His|Met|Val|Ile<br>315|Val|Val|Ala|Glu|Gly<br>320|
|Ala|Gly|Gln|Glu|Leu<br>325|Leu|Ala|Ala|Glu|Asn<br>330|Leu|Lys|Thr|Ser|Thr<br>335|Ala|
|Lys|Asp|Ala|Ser<br>340|Gly|Asn|Lys|Leu|Leu<br>345|His|Asp|Val|Gly|Leu<br>350|Trp|Ile|
|Ser|Asp|Lys<br>355|Ile|Lys|Ala|His|Phe<br>360|Ala|Lys|Ile|Pro|Pro<br>365|Met|Pro|Ile|
|Thr|Leu<br>370|Lys|Tyr|Ile|Asp|Pro<br>375|Thr|Tyr|Met|Ile|Arg<br>380|Ala|Val|Pro|Ser|
|Asn<br>385|Ala|Ser|Asp|Asn|Val<br>390|Tyr|Cys|Thr|Leu|Leu<br>395|Ala|Gln|Ser|Cys|Val<br>400|
|His|Gly|Val|Met|Ala<br>405|Gly|Tyr|Thr|Gly|Phe<br>410|Thr|Ser|Gly|Leu|Val<br>415|Asn|
|Gly|Arg|Gln|Thr<br>420|Tyr|Ile|Pro|Phe|Asn<br>425|Arg|Ile|Thr|Glu|Lys<br>430|Gln|Asn|
|Asn|Val|Val<br>435|Ile|Thr|Asp|Arg|Met<br>440|Trp|Ala|Arg|Leu|Leu<br>445|Ser|Ser|Thr|
|Asn|Gln<br>450|Pro|Ser|Phe|Leu|Arg<br>455|Pro|Gln|Asp|Val|Ile<br>460|Glu|Val|Gln|Lys|
|Gln<br>465|Glu|Glu|Pro|Pro|Ser<br>470|Gln|Leu|Leu|Asp|Gly<br>475|Asp|Ser|Ser|Lys|Pro<br>480|
|Asn|Asp|Ile| | | | | | | | | | | | | |

( 2 ) INFORMATION FOR SEQ ID NO:5:

( i ) SEQUENCE CHARACTERISTICS:
        ( A ) LENGTH: 1624 base pairs ( B ) TYPE: nucleic acid
( C ) STRANDEDNESS: double
( D ) TOPOLOGY: linear ( i i ) MOLECULE TYPE: cDNA to mRNA ( i x ) FEATURE:
( A ) NAME/KEY: CDS
( B ) LOCATION: 3..1409

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| TG | GTA | GTC | GCA | CAC | ATG | CGG | CAC | GTC | CTC | GAT | CTA | CCG | ACA | TAC | TCA | 47 |
|    | Val | Val | Ala | His | Met | Arg | His | Val | Leu | Asp | Leu | Pro | Thr | Tyr | Ser |    |
|    | 1   |     |     |     | 5   |     |     |     | 10  |     |     |     |     | 15  |     |    |
| AAT | CCA | CTG | CAA | GAT | AAC | CCG | GCA | TAC | TCG | GTT | GTG | AAG | CAA | TAC | TTT | 95 |
| Asn | Pro | Leu | Gln | Asp | Asn | Pro | Ala | Tyr | Ser | Val | Val | Lys | Gln | Tyr | Phe |    |
|     |     |     |     | 20  |     |     |     |     | 25  |     |     |     |     | 30  |     |    |
| GTA | AAC | CCA | GAT | GAC | ACT | GTC | TGC | CAG | AAG | GCC | ATT | GTT | CAC | AAG | GAT | 143 |
| Val | Asn | Pro | Asp | Asp | Thr | Val | Cys | Gln | Lys | Ala | Ile | Val | His | Lys | Asp |    |
|     |     |     | 35  |     |     |     |     | 40  |     |     |     |     | 45  |     |     |    |
| GGC | CCT | AGA | GGC | AAC | CAC | TTC | CGT | CGT | GCT | GGG | CCT | CGA | CAG | AGG | GTG | 191 |
| Gly | Pro | Arg | Gly | Asn | His | Phe | Arg | Arg | Ala | Gly | Pro | Arg | Gln | Arg | Val |    |
|     |     | 50  |     |     |     |     | 55  |     |     |     |     | 60  |     |     |     |    |
| TTT | TTT | GAA | TCG | GAT | GAG | GTC | CAT | GCA | TGC | ATT | GTC | ACA | TGT | GGA | GGA | 239 |
| Phe | Phe | Glu | Ser | Asp | Glu | Val | His | Ala | Cys | Ile | Val | Thr | Cys | Gly | Gly |    |
|     | 65  |     |     |     |     | 70  |     |     |     |     | 75  |     |     |     |     |    |
| CTG | TGC | CCT | GGA | CTG | AAC | ACT | GTC | ATT | AGG | GAA | ATT | GTT | TGT | GGC | CTA | 287 |
| Leu | Cys | Pro | Gly | Leu | Asn | Thr | Val | Ile | Arg | Glu | Ile | Val | Cys | Gly | Leu |    |
| 80  |     |     |     |     | 85  |     |     |     |     | 90  |     |     |     |     | 95  |    |
| AAT | GAC | ATG | TAT | GGT | GTC | AGT | AGG | GTA | CTT | GGA | ATT | CAG | GGT | GGG | TAT | 335 |
| Asn | Asp | Met | Tyr | Gly | Val | Ser | Arg | Val | Leu | Gly | Ile | Gln | Gly | Gly | Tyr |    |
|     |     |     |     | 100 |     |     |     |     | 105 |     |     |     |     | 110 |     |    |
| AGA | GGT | TTC | TAT | GCT | TGT | AAC | ACC | ATT | GAC | TTG | AGT | CCA | AAG | AGT | GTA | 383 |
| Arg | Gly | Phe | Tyr | Ala | Cys | Asn | Thr | Ile | Asp | Leu | Ser | Pro | Lys | Ser | Val |    |
|     |     |     | 115 |     |     |     |     | 120 |     |     |     |     | 125 |     |     |    |
| AAC | GAC | AAT | CAC | AAA | AGG | GGT | GGA | ACT | GTT | CTT | GGG | ACA | TCA | CGT | GGA | 431 |
| Asn | Asp | Asn | His | Lys | Arg | Gly | Gly | Thr | Val | Leu | Gly | Thr | Ser | Arg | Gly |    |
|     |     | 130 |     |     |     |     | 135 |     |     |     |     | 140 |     |     |     |    |
| GGC | CAT | GAC | ACC | ATG | AAG | ATT | GTT | GAC | AGC | ATC | CAG | GAT | CGT | GGT | ATA | 479 |
| Gly | His | Asp | Thr | Met | Lys | Ile | Val | Asp | Ser | Ile | Gln | Asp | Arg | Gly | Ile |    |
|     | 145 |     |     |     |     | 150 |     |     |     |     | 155 |     |     |     |     |    |
| AAT | CAG | GTT | TAT | GTA | ATT | GGT | GGT | GAT | GGT | ACT | CAA | AGG | GGT | GCA | GGA | 527 |
| Asn | Gln | Val | Tyr | Val | Ile | Gly | Gly | Asp | Gly | Thr | Gln | Arg | Gly | Ala | Gly |    |
| 160 |     |     |     |     | 165 |     |     |     |     | 170 |     |     |     |     | 175 |    |
| GTG | ATT | TTT | GAA | GAG | ATT | AGA | AGA | CGT | GGT | CTC | AAG | GTT | GCT | GTT | GCT | 575 |
| Val | Ile | Phe | Glu | Glu | Ile | Arg | Arg | Arg | Gly | Leu | Lys | Val | Ala | Val | Ala |    |
|     |     |     |     | 180 |     |     |     |     | 185 |     |     |     |     | 190 |     |    |
| GGC | ATT | CCA | AAG | ACG | ATT | GAT | AAT | GAT | ATA | CCA | GTA | ATT | GAC | AGA | TCA | 623 |
| Gly | Ile | Pro | Lys | Thr | Ile | Asp | Asn | Asp | Ile | Pro | Val | Ile | Asp | Arg | Ser |    |
|     |     |     | 195 |     |     |     |     | 200 |     |     |     |     | 205 |     |     |    |
| TTT | GGT | TTC | GAC | ACT | GCA | GTT | GAG | GAG | GCC | CAA | CGT | GCA | ATA | AAT | GCT | 671 |
| Phe | Gly | Phe | Asp | Thr | Ala | Val | Glu | Glu | Ala | Gln | Arg | Ala | Ile | Asn | Ala |    |
|     |     |     | 210 |     |     |     |     | 215 |     |     |     |     | 220 |     |     |    |
| GCT | CAT | GTA | GAA | GCT | GGA | AGC | GCC | GAG | AAT | GGT | ATA | GGC | CTC | GTA | AAG | 719 |
| Ala | His | Val | Glu | Ala | Gly | Ser | Ala | Glu | Asn | Gly | Ile | Gly | Leu | Val | Lys |    |
|     | 225 |     |     |     |     | 230 |     |     |     |     | 235 |     |     |     |     |    |
| CTA | ATG | GGT | CGA | CAC | AGT | GGT | TTT | ATT | GCA | CAC | TAT | GCT | ACT | CTA | GCC | 767 |
| Leu | Met | Gly | Arg | His | Ser | Gly | Phe | Ile | Ala | His | Tyr | Ala | Thr | Leu | Ala |    |
| 240 |     |     |     |     | 245 |     |     |     |     | 250 |     |     |     |     | 255 |    |
| AGC | AGA | GAC | GTG | GAT | TGT | TGT | TTG | ATT | CCA | GAG | TCA | CCT | TTC | TAT | CTG | 815 |
| Ser | Arg | Asp | Val | Asp | Cys | Cys | Leu | Ile | Pro | Glu | Ser | Pro | Phe | Tyr | Leu |    |
|     |     |     |     | 260 |     |     |     |     | 265 |     |     |     |     | 270 |     |    |

| | | | | | | | | | | | | | | | | |
|---|---|---|---|---|---|---|---|---|---|---|---|---|---|---|---|---|
| GAA | GGT | GAA | GGT | GGC | CTT | TTT | AGA | TAT | TTG | GAA | AAG | CGT | CTG | AAG | GAG | 863 |
| Glu | Gly | Glu | Gly | Gly | Leu | Phe | Arg | Tyr | Leu | Glu | Lys | Arg | Leu | Lys | Glu | |
| | | | | 275 | | | | 280 | | | | | 285 | | | |
| AAT | GGT | CAT | ATG | GTT | ATC | GTT | GTT | GCG | GAG | GGT | GCA | GGG | CAG | AAA | CTT | 911 |
| Asn | Gly | His | Met | Val | Ile | Val | Val | Ala | Glu | Gly | Ala | Gly | Gln | Lys | Leu | |
| | | 290 | | | | 295 | | | | | 300 | | | | | |
| ATT | AAT | GAA | ACA | AAG | GAA | TCA | ATG | GGG | AAA | GAT | GCT | TCA | GGC | AAT | TCG | 959 |
| Ile | Asn | Glu | Thr | Lys | Glu | Ser | Met | Gly | Lys | Asp | Ala | Ser | Gly | Asn | Ser | |
| 305 | | | | | | 310 | | | | | 315 | | | | | |
| ATT | CTT | CTT | GAT | GTT | GGT | CTT | TGG | TTA | TCT | CAA | AAG | ATA | AAA | GAG | CAT | 1007 |
| Ile | Leu | Leu | Asp | Val | Gly | Leu | Trp | Leu | Ser | Gln | Lys | Ile | Lys | Glu | His | |
| 320 | | | | | 325 | | | | | 330 | | | | | 335 | |
| TTC | AAG | AAA | ATC | AAG | ACT | ACT | ATA | AAT | CTC | AAG | TAT | ATA | GAT | CCT | ACA | 1055 |
| Phe | Lys | Lys | Ile | Lys | Thr | Thr | Ile | Asn | Leu | Lys | Tyr | Ile | Asp | Pro | Thr | |
| | | | | 340 | | | | | 345 | | | | | 350 | | |
| TAC | ATG | ATA | CGT | GCC | ATT | CCT | AGC | AAT | GCA | TCT | GAC | AAT | GTG | TAT | TGC | 1103 |
| Tyr | Met | Ile | Arg | Ala | Ile | Pro | Ser | Asn | Ala | Ser | Asp | Asn | Val | Tyr | Cys | |
| | | | 355 | | | | | 360 | | | | | 365 | | | |
| ACA | CTG | TTG | GCA | CAC | AGG | GTG | GTT | CAT | GGA | GCC | ATG | GCT | GGA | TAC | ACT | 1151 |
| Thr | Leu | Leu | Ala | His | Arg | Val | Val | His | Gly | Ala | Met | Ala | Gly | Tyr | Thr | |
| | | 370 | | | | 375 | | | | | 380 | | | | | |
| GGT | TTC | ACT | GTT | GGC | CAA | GTA | AAT | GGT | CGG | CAT | TGC | TAT | ATC | CCG | TTT | 1199 |
| Gly | Phe | Thr | Val | Gly | Gln | Val | Asn | Gly | Arg | His | Cys | Tyr | Ile | Pro | Phe | |
| 385 | | | | | 390 | | | | | 395 | | | | | | |
| TAC | AGG | ATC | ACA | GAG | AAG | CAG | AAC | AAA | GTT | TCA | ATT | ACT | GAT | AGG | ATG | 1247 |
| Tyr | Arg | Ile | Thr | Glu | Lys | Gln | Asn | Lys | Val | Ser | Ile | Thr | Asp | Arg | Met | |
| 400 | | | | | 405 | | | | | 410 | | | | | 415 | |
| TGG | GCA | AGA | CTT | CTC | TCC | TCA | ACC | AAC | CAG | CCA | AGT | TTC | CTC | AGC | AAG | 1295 |
| Trp | Ala | Arg | Leu | Leu | Ser | Ser | Thr | Asn | Gln | Pro | Ser | Phe | Leu | Ser | Lys | |
| | | | | 420 | | | | | 425 | | | | | 430 | | |
| AAA | GAT | GTG | GAG | GAC | GCA | AAG | ATG | GAA | GAA | GAG | AGA | GCA | TCC | AAG | TTT | 1343 |
| Lys | Asp | Val | Glu | Asp | Ala | Lys | Met | Glu | Glu | Glu | Arg | Ala | Ser | Lys | Phe | |
| | | | 435 | | | | | 440 | | | | | 445 | | | |
| TTC | GAT | GGC | CCG | CCT | CCC | AAC | CCC | AAG | GTT | GAA | GAC | AAA | GTC | GCT | TCC | 1391 |
| Phe | Asp | Gly | Pro | Pro | Pro | Asn | Pro | Lys | Val | Glu | Asp | Lys | Val | Ala | Ser | |
| | | | 450 | | | | | 455 | | | | | 460 | | | |
| AAT | GGC | AAG | GCT | GTG | AAG | TGAGGCAGAA | GGCTACTGAT | CTATTATGTG | | | | | | | | 1439 |
| Asn | Gly | Lys | Ala | Val | Lys | | | | | | | | | | | |
| 465 | | | | | | | | | | | | | | | | |

CAGATGGATT AATTATTACT CAATAATGTC AGTAATCTAT CTATGGCTAG TGAGATGGAT 1499

TAGTAAATAA TATTAGTATA TCTATGGCAA GTGATGCTCA GCTCTTCCTG TCCAAATTAA 1559

AATGCCGAGA ATAGATCTCC TCTAGCAGGT TATCGTCATT ATATTTAAAA AAAAAAAAAA 1619

AAAAA 1624

( 2 ) INFORMATION FOR SEQ ID NO:6:

( i ) SEQUENCE CHARACTERISTICS:
        ( A ) LENGTH: 469 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Val | Val | Ala | His | Met | Arg | His | Val | Leu | Asp | Leu | Pro | Thr | Tyr | Ser | Asn |
| 1 | | | | 5 | | | | | 10 | | | | | 15 | |

| | | | | | | | | | | | | | | |
|---|---|---|---|---|---|---|---|---|---|---|---|---|---|---|
| Pro | Leu | Gln | Asp | Asn | Pro | Ala | Tyr | Ser | Val | Val | Lys | Gln | Tyr | Phe | Val |
| | | | | 20 | | | | 25 | | | | | 30 | | |

| | | | | | | | | | | | | | | |
|---|---|---|---|---|---|---|---|---|---|---|---|---|---|---|
| Asn | Pro | Asp | Asp | Thr | Val | Cys | Gln | Lys | Ala | Ile | Val | His | Lys | Asp | Gly |
| | | | 35 | | | | | 40 | | | | | 45 | | |

```
Pro  Arg  Gly  Asn  His  Phe  Arg  Arg  Ala  Gly  Pro  Arg  Gln  Arg  Val  Phe
     50                  55                  60
Phe  Glu  Ser  Asp  Glu  Val  His  Ala  Cys  Ile  Val  Thr  Cys  Gly  Gly  Leu
65                       70                  75                            80
Cys  Pro  Gly  Leu  Asn  Thr  Val  Ile  Arg  Glu  Ile  Val  Cys  Gly  Leu  Asn
                    85                  90                            95
Asp  Met  Tyr  Gly  Val  Ser  Arg  Val  Leu  Gly  Ile  Gln  Gly  Gly  Tyr  Arg
              100                      105                      110
Gly  Phe  Tyr  Ala  Cys  Asn  Thr  Ile  Asp  Leu  Ser  Pro  Lys  Ser  Val  Asn
          115                      120                 125
Asp  Asn  His  Lys  Arg  Gly  Gly  Thr  Val  Leu  Gly  Thr  Ser  Arg  Gly  Gly
     130                      135                      140
His  Asp  Thr  Met  Lys  Ile  Val  Asp  Ser  Ile  Gln  Asp  Arg  Gly  Ile  Asn
145                      150                      155                      160
Gln  Val  Tyr  Val  Ile  Gly  Gly  Asp  Gly  Thr  Gln  Arg  Gly  Ala  Gly  Val
                    165                      170                      175
Ile  Phe  Glu  Glu  Ile  Arg  Arg  Arg  Gly  Leu  Lys  Val  Ala  Val  Ala  Gly
              180                      185                      190
Ile  Pro  Lys  Thr  Ile  Asp  Asn  Asp  Ile  Pro  Val  Ile  Asp  Arg  Ser  Phe
          195                      200                      205
Gly  Phe  Asp  Thr  Ala  Val  Glu  Glu  Ala  Gln  Arg  Ala  Ile  Asn  Ala  Ala
     210                      215                      220
His  Val  Glu  Ala  Gly  Ser  Ala  Glu  Asn  Gly  Ile  Gly  Leu  Val  Lys  Leu
225                      230                      235                      240
Met  Gly  Arg  His  Ser  Gly  Phe  Ile  Ala  His  Tyr  Ala  Thr  Leu  Ala  Ser
                    245                      250                      255
Arg  Asp  Val  Asp  Cys  Cys  Leu  Ile  Pro  Glu  Ser  Pro  Phe  Tyr  Leu  Glu
              260                      265                      270
Gly  Glu  Gly  Gly  Leu  Phe  Arg  Tyr  Leu  Glu  Lys  Arg  Leu  Lys  Glu  Asn
          275                      280                      285
Gly  His  Met  Val  Ile  Val  Val  Ala  Glu  Gly  Ala  Gly  Gln  Lys  Leu  Ile
     290                      295                      300
Asn  Glu  Thr  Lys  Glu  Ser  Met  Gly  Lys  Asp  Ala  Ser  Gly  Asn  Ser  Ile
305                      310                      315                      320
Leu  Leu  Asp  Val  Gly  Leu  Trp  Leu  Ser  Gln  Lys  Ile  Lys  Glu  His  Phe
                    325                      330                      335
Lys  Lys  Ile  Lys  Thr  Thr  Ile  Asn  Leu  Lys  Tyr  Ile  Asp  Pro  Thr  Tyr
              340                      345                      350
Met  Ile  Arg  Ala  Ile  Pro  Ser  Asn  Ala  Ser  Asp  Asn  Val  Tyr  Cys  Thr
          355                      360                      365
Leu  Leu  Ala  His  Arg  Val  Val  His  Gly  Ala  Met  Ala  Gly  Tyr  Thr  Gly
     370                      375                      380
Phe  Thr  Val  Gly  Gln  Val  Asn  Gly  Arg  His  Cys  Tyr  Ile  Pro  Phe  Tyr
385                      390                      395                      400
Arg  Ile  Thr  Glu  Lys  Gln  Asn  Lys  Val  Ser  Ile  Thr  Asp  Arg  Met  Trp
                    405                      410                      415
Ala  Arg  Leu  Leu  Ser  Ser  Thr  Asn  Gln  Pro  Ser  Phe  Leu  Ser  Lys  Lys
              420                      425                      430
Asp  Val  Glu  Asp  Ala  Lys  Met  Glu  Glu  Glu  Arg  Ala  Ser  Lys  Phe  Phe
          435                      440                      445
Asp  Gly  Pro  Pro  Pro  Asn  Pro  Lys  Val  Glu  Asp  Lys  Val  Ala  Ser  Asn
     450                      455                      460
```

Gly Lys Ala Val Lys
465

( 2 ) INFORMATION FOR SEQ ID NO:7:

( i ) SEQUENCE CHARACTERISTICS:
        ( A ) LENGTH: 2048 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 121..1686

( x i ) SEQUENCE DESCRIPTION: SEQ ID NO:7:

```
CGAACCCGAA  CCCTCCAAGC  CGGCAGGCCG  GAGCAGAGCG  CGCTCCAAGC  TGAATCCCCC    60

CATCTCCTAT  CGCCGTCGAA  AGCCGCAGGT  CCATTATAAC  TTTTTATGAC  CTTGTCTGGG   120

ATG GCT GTT GCT TTC AAA GCA AGT ACA AGT TCT GTC ACA CAG CAA CAT         168
Met Ala Val Ala Phe Lys Ala Ser Thr Ser Ser Val Thr Gln Gln His
 1               5                  10                  15

TGG TCA AGT CCA ACA AAG GAC CAG TGT CAA TAT GGT TTC ACT CAT TTA         216
Trp Ser Ser Pro Thr Lys Asp Gln Cys Gln Tyr Gly Phe Thr His Leu
            20                  25                  30

AGC AGG CAA AAG TGC AGA AAA AGA GCA CTG TGT GTG ACA GCT ATA TCA         264
Ser Arg Gln Lys Cys Arg Lys Arg Ala Leu Cys Val Thr Ala Ile Ser
        35                  40                  45

GGG AAG CTA GAC CTA GAT TTC ACT GAT CCT TCT TGG AAC CAA AAG TAC         312
Gly Lys Leu Asp Leu Asp Phe Thr Asp Pro Ser Trp Asn Gln Lys Tyr
    50                  55                  60

CAG GAA GAC TGG AAC AGG CGT TTT AGT TTG CCA CAT ATT AAT GAT ATA         360
Gln Glu Asp Trp Asn Arg Arg Phe Ser Leu Pro His Ile Asn Asp Ile
65                  70                  75                  80

TAT GAT TTG GAA CCA AGA AGA ACT ACA TTC TCT TTG AAG AAA AAC AGA         408
Tyr Asp Leu Glu Pro Arg Arg Thr Thr Phe Ser Leu Lys Lys Asn Arg
                85                  90                  95

ATT CCC CTG GGT GAT GGT GAT GGC TCA TCA ACT GAT ATG TGG AAC GGT         456
Ile Pro Leu Gly Asp Gly Asp Gly Ser Ser Thr Asp Met Trp Asn Gly
            100                 105                 110

TAT GTA AAT AAG AAT GAT AGA GCC CTT TTG AAG GTG ATA AAG TAT GCA         504
Tyr Val Asn Lys Asn Asp Arg Ala Leu Leu Lys Val Ile Lys Tyr Ala
        115                 120                 125

TCT CCT ACT TCT GCT GGA GCT GAG TGC ATT GAT CCT GAT TGT AGC TGG         552
Ser Pro Thr Ser Ala Gly Ala Glu Cys Ile Asp Pro Asp Cys Ser Trp
    130                 135                 140

GTG GAA CAC TGG GTT CAT CGT GCA GGT CCT CGT AAG GAG ATA TAT TAC         600
Val Glu His Trp Val His Arg Ala Gly Pro Arg Lys Glu Ile Tyr Tyr
145                 150                 155                 160

GAA CCT GAA GAA GTA AAG GCT GCC ATT GTT ACC TGT GGA GGG CTC TGT         648
Glu Pro Glu Glu Val Lys Ala Ala Ile Val Thr Cys Gly Gly Leu Cys
                165                 170                 175

CCT GGT CTA AAT GAT GTC ATT AGG CAG ATA GTA TTT ACT TTG GAG ACT         696
Pro Gly Leu Asn Asp Val Ile Arg Gln Ile Val Phe Thr Leu Glu Thr
            180                 185                 190

TAT GGG GTG AAG AAT ATT GTT GGA ATC CCA TTT GGT TAT CGT GGA TTT         744
Tyr Gly Val Lys Asn Ile Val Gly Ile Pro Phe Gly Tyr Arg Gly Phe
        195                 200                 205

TTT GAG AAA GGC TTA AAA GAA ATG CCG CTC TCG CGT GAC GTG GTG GAA         792
Phe Glu Lys Gly Leu Lys Glu Met Pro Leu Ser Arg Asp Val Val Glu
    210                 215                 220
```

| | | | | | | | | | | | | | | | | |
|---|---|---|---|---|---|---|---|---|---|---|---|---|---|---|---|---|
| AAC | ATA | AAT | CTT | TCT | GGA | GGA | AGT | TTC | CTA | GGA | GTC | TCT | CGT | GGA | GGA | 840 |
| Asn | Ile | Asn | Leu | Ser | Gly | Gly | Ser | Phe | Leu | Gly | Val | Ser | Arg | Gly | Gly | |
| 225 | | | | 230 | | | | | 235 | | | | | | 240 | |
| GCT | AAA | ACT | AGT | GAG | ATT | GTA | GAT | AGC | ATA | CAA | GCC | AGA | AGA | ATT | GAC | 888 |
| Ala | Lys | Thr | Ser | Glu | Ile | Val | Asp | Ser | Ile | Gln | Ala | Arg | Arg | Ile | Asp | |
| | | | | 245 | | | | | 250 | | | | | | 255 | |
| ATG | CTA | TTT | GTA | ATT | GGT | GGA | AAT | GGT | AGC | CAT | GCA | GGA | GCT | AAT | GCT | 936 |
| Met | Leu | Phe | Val | Ile | Gly | Gly | Asn | Gly | Ser | His | Ala | Gly | Ala | Asn | Ala | |
| | | | 260 | | | | | 265 | | | | | 270 | | | |
| ATT | CAT | GAG | GAG | TGT | CGA | AAG | AGA | AAA | CTG | AAA | GTT | TCA | GTT | GTA | GCA | 984 |
| Ile | His | Glu | Glu | Cys | Arg | Lys | Arg | Lys | Leu | Lys | Val | Ser | Val | Val | Ala | |
| | | 275 | | | | | 280 | | | | | 285 | | | | |
| GTC | CCA | AAG | ACA | ATT | GAT | AAT | GAT | ATA | CTT | TTT | ATG | GAT | AAG | ACG | TTT | 1032 |
| Val | Pro | Lys | Thr | Ile | Asp | Asn | Asp | Ile | Leu | Phe | Met | Asp | Lys | Thr | Phe | |
| | 290 | | | | | 295 | | | | | 300 | | | | | |
| GGT | TTT | GAT | ACA | GCT | GTA | GAG | AAA | GCT | CAG | CGT | GCT | ATC | AAT | TCT | GCC | 1080 |
| Gly | Phe | Asp | Thr | Ala | Val | Glu | Lys | Ala | Gln | Arg | Ala | Ile | Asn | Ser | Ala | |
| 305 | | | | | 310 | | | | | 315 | | | | | 320 | |
| TAT | ATA | GAG | GCA | CGT | AGT | GCA | TAC | CAC | GGA | ATT | GGG | TTA | GTA | AAA | TTA | 1128 |
| Tyr | Ile | Glu | Ala | Arg | Ser | Ala | Tyr | His | Gly | Ile | Gly | Leu | Val | Lys | Leu | |
| | | | | 325 | | | | | 330 | | | | | 335 | | |
| ATG | GGA | AGA | AGT | AGT | GGA | TTC | ATA | GCC | ATG | CAT | GCT | TCT | CTT | TCC | AGT | 1176 |
| Met | Gly | Arg | Ser | Ser | Gly | Phe | Ile | Ala | Met | His | Ala | Ser | Leu | Ser | Ser | |
| | | | 340 | | | | | 345 | | | | | 350 | | | |
| GGA | CAG | ATT | GAT | GTT | TGC | CTG | ATA | CCT | GAG | GTA | TCC | TTC | ACA | CTT | GAT | 1224 |
| Gly | Gln | Ile | Asp | Val | Cys | Leu | Ile | Pro | Glu | Val | Ser | Phe | Thr | Leu | Asp | |
| | | 355 | | | | | 360 | | | | | 365 | | | | |
| GGA | GAA | CAT | GGT | GTC | TTG | CGA | CAC | CTT | GAG | CAT | TTA | CTT | AAT | ACA | AAG | 1272 |
| Gly | Glu | His | Gly | Val | Leu | Arg | His | Leu | Glu | His | Leu | Leu | Asn | Thr | Lys | |
| | 370 | | | | | 375 | | | | | 380 | | | | | |
| GGA | TTT | TGT | GTG | GTT | TGT | GTT | GCT | GAA | GGT | GCA | GGG | CAG | GAT | TTA | CTC | 1320 |
| Gly | Phe | Cys | Val | Val | Cys | Val | Ala | Glu | Gly | Ala | Gly | Gln | Asp | Leu | Leu | |
| 385 | | | | | 390 | | | | | 395 | | | | | 400 | |
| CAA | AAA | TCA | AAT | GCA | ACT | GAC | GCT | TCA | GGA | AAT | GTG | ATA | CTT | AGT | GAC | 1368 |
| Gln | Lys | Ser | Asn | Ala | Thr | Asp | Ala | Ser | Gly | Asn | Val | Ile | Leu | Ser | Asp | |
| | | | | 405 | | | | | 410 | | | | | 415 | | |
| TTT | GGT | GTC | CAC | ATG | CAG | CAG | AAG | ATC | AAG | AAG | CAT | TTC | AAG | GAC | ATC | 1416 |
| Phe | Gly | Val | His | Met | Gln | Gln | Lys | Ile | Lys | Lys | His | Phe | Lys | Asp | Ile | |
| | | | 420 | | | | | 425 | | | | | 430 | | | |
| GGT | GTT | CCC | GCT | GAT | CTA | AAA | TAC | ATT | GAT | CCA | ACA | TAT | ATG | GTT | CGG | 1464 |
| Gly | Val | Pro | Ala | Asp | Leu | Lys | Tyr | Ile | Asp | Pro | Thr | Tyr | Met | Val | Arg | |
| | | 435 | | | | | 440 | | | | | 445 | | | | |
| GCC | TGC | CGG | GCA | AAT | GCA | TCT | GAT | GCT | ATT | CTC | TGC | ACC | GTA | CTT | GGG | 1512 |
| Ala | Cys | Arg | Ala | Asn | Ala | Ser | Asp | Ala | Ile | Leu | Cys | Thr | Val | Leu | Gly | |
| | 450 | | | | | 455 | | | | | 460 | | | | | |
| CAA | AAT | GCT | GTC | CAT | GGA | GCA | TTT | GCT | GGG | TTC | AGT | GGC | ATC | ACG | TCA | 1560 |
| Gln | Asn | Ala | Val | His | Gly | Ala | Phe | Ala | Gly | Phe | Ser | Gly | Ile | Thr | Ser | |
| 465 | | | | | 470 | | | | | 475 | | | | | 480 | |
| GGT | GTT | TGC | AAC | ACA | CAT | TAT | GTC | TAC | CTT | CCC | ATC | ACA | GAG | GTC | ATT | 1608 |
| Gly | Val | Cys | Asn | Thr | His | Tyr | Val | Tyr | Leu | Pro | Ile | Thr | Glu | Val | Ile | |
| | | | | 485 | | | | | 490 | | | | | 495 | | |
| ACA | ACA | CCA | AAG | CAC | GTC | AAC | CCC | AAC | AGC | AGA | ATG | TGG | CAC | CGC | TGC | 1656 |
| Thr | Thr | Pro | Lys | His | Val | Asn | Pro | Asn | Ser | Arg | Met | Trp | His | Arg | Cys | |
| | | | 500 | | | | | 505 | | | | | 510 | | | |
| CTC | ACA | TCC | ACT | GGC | CAG | CCA | GAC | TTC | CAT | TGACTACTTC | ATTAACACCT | | | | | 1706 |
| Leu | Thr | Ser | Thr | Gly | Gln | Pro | Asp | Phe | His | | | | | | | |
| | | 515 | | | | | 520 | | | | | | | | | |

GAGAGCAAGG CGCCAGGAGA ATATTTAATC CCACAAGGGA CTGCTAACAG GAACTTGAAT    1766

AAATCTGGCT AACCCAAAAT TTTGTGAGGC TGGAGGAGCT CATAACGAAA TTGCCAGAGC    1826

| | | | | | | | | | | |
|---|---|---|---|---|---|---|---|---|---|---|
| CACCCCCTGG | TCATCCAGAC | GTTGTAAGCA | TGCATACCCT | TTCTAGTGGT | TTGCAATCCC | 1886 |
| AAGTGAAATT | AAAAGTTAGG | AGTTGTTTGT | TCTCCAAACA | ATTCACCATA | ATCCACCAG | 1946 |
| CACCAAACTG | GCTCCAGCCT | TGTGAGATGT | TTTATTGATG | ATGTACTATG | CATAATAGGC | 2006 |
| AATTGGATAT | TCTTACTGGG | AAAAAAAAAA | AAAAAAAAAA | AA | | 2048 |

(2) INFORMATION FOR SEQ ID NO:8:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Val Ala Phe Lys Ala Ser Thr Ser Val Thr Gln Gln His
 1               5                  10                  15

Trp Ser Ser Pro Thr Lys Asp Gln Cys Gln Tyr Gly Phe Thr His Leu
            20                  25                  30

Ser Arg Gln Lys Cys Arg Lys Arg Ala Leu Cys Val Thr Ala Ile Ser
        35                  40                      45

Gly Lys Leu Asp Leu Asp Phe Thr Asp Pro Ser Trp Asn Gln Lys Tyr
    50                      55                  60

Gln Glu Asp Trp Asn Arg Arg Phe Ser Leu Pro His Ile Asn Asp Ile
65                  70                  75                      80

Tyr Asp Leu Glu Pro Arg Arg Thr Thr Phe Ser Leu Lys Lys Asn Arg
                85                  90                  95

Ile Pro Leu Gly Asp Gly Asp Gly Ser Ser Thr Asp Met Trp Asn Gly
                100                 105                 110

Tyr Val Asn Lys Asn Asp Arg Ala Leu Leu Lys Val Ile Lys Tyr Ala
            115                 120                 125

Ser Pro Thr Ser Ala Gly Ala Glu Cys Ile Asp Pro Asp Cys Ser Trp
        130                 135                 140

Val Glu His Trp Val His Arg Ala Gly Pro Arg Lys Glu Ile Tyr Tyr
145                 150                 155                 160

Glu Pro Glu Glu Val Lys Ala Ala Ile Val Thr Cys Gly Gly Leu Cys
                165                 170                 175

Pro Gly Leu Asn Asp Val Ile Arg Gln Ile Val Phe Thr Leu Glu Thr
                180                 185                 190

Tyr Gly Val Lys Asn Ile Val Gly Ile Pro Phe Gly Tyr Arg Gly Phe
            195                 200                 205

Phe Glu Lys Gly Leu Lys Glu Met Pro Leu Ser Arg Asp Val Val Glu
210                 215                 220

Asn Ile Asn Leu Ser Gly Gly Ser Phe Leu Gly Val Ser Arg Gly Gly
225                 230                 235                 240

Ala Lys Thr Ser Glu Ile Val Asp Ser Ile Gln Ala Arg Arg Ile Asp
                245                 250                 255

Met Leu Phe Val Ile Gly Gly Asn Gly Ser His Ala Gly Ala Asn Ala
            260                 265                 270

Ile His Glu Glu Cys Arg Lys Arg Lys Leu Lys Val Ser Val Val Ala
        275                 280                 285

Val Pro Lys Thr Ile Asp Asn Asp Ile Leu Phe Met Asp Lys Thr Phe
    290                 295                 300

Gly Phe Asp Thr Ala Val Glu Lys Ala Gln Arg Ala Ile Asn Ser Ala
305                 310                 315                 320
```

```
Tyr  Ile  Glu  Ala  Arg  Ser  Ala  Tyr  His  Gly  Ile  Gly  Leu  Val  Lys  Leu
               325                     330                     335

Met  Gly  Arg  Ser  Ser  Gly  Phe  Ile  Ala  Met  His  Ala  Ser  Leu  Ser  Ser
               340                     345                     350

Gly  Gln  Ile  Asp  Val  Cys  Leu  Ile  Pro  Glu  Val  Ser  Phe  Thr  Leu  Asp
          355                     360                     365

Gly  Glu  His  Gly  Val  Leu  Arg  His  Leu  Glu  His  Leu  Leu  Asn  Thr  Lys
     370                     375                     380

Gly  Phe  Cys  Val  Val  Cys  Val  Ala  Glu  Gly  Ala  Gly  Gln  Asp  Leu  Leu
385                      390                     395                     400

Gln  Lys  Ser  Asn  Ala  Thr  Asp  Ala  Ser  Gly  Asn  Val  Ile  Leu  Ser  Asp
                    405                     410                     415

Phe  Gly  Val  His  Met  Gln  Gln  Lys  Ile  Lys  Lys  His  Phe  Lys  Asp  Ile
               420                     425                     430

Gly  Val  Pro  Ala  Asp  Leu  Lys  Tyr  Ile  Asp  Pro  Thr  Tyr  Met  Val  Arg
               435                     440                     445

Ala  Cys  Arg  Ala  Asn  Ala  Ser  Asp  Ala  Ile  Leu  Cys  Thr  Val  Leu  Gly
     450                     455                     460

Gln  Asn  Ala  Val  His  Gly  Ala  Phe  Ala  Gly  Phe  Ser  Gly  Ile  Thr  Ser
465                      470                     475                     480

Gly  Val  Cys  Asn  Thr  His  Tyr  Val  Tyr  Leu  Pro  Ile  Thr  Glu  Val  Ile
                    485                     490                     495

Thr  Thr  Pro  Lys  His  Val  Asn  Pro  Asn  Ser  Arg  Met  Trp  His  Arg  Cys
               500                     505                     510

Leu  Thr  Ser  Thr  Gly  Gln  Pro  Asp  Phe  His
               515                     520
```

( 2 ) INFORMATION FOR SEQ ID NO:9:

( i ) SEQUENCE CHARACTERISTICS:
        ( A ) LENGTH: 1558 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..1278

( x i ) SEQUENCE DESCRIPTION: SEQ ID NO:9:

```
TCT  GTT  GTT  AAG  CAG  TAC  TTC  GTT  GAT  GAG  GAT  GAC  ACG  GTT  CCT  CAG     48
Ser  Val  Val  Lys  Gln  Tyr  Phe  Val  Asp  Glu  Asp  Asp  Thr  Val  Pro  Gln
 1                    5                     10                    15

AAG  ATC  GTT  GTT  CAT  CCT  GAT  AGT  CCA  AGA  GGA  ACA  CAT  TTC  CGC  AGA     96
Lys  Ile  Val  Val  His  Pro  Asp  Ser  Pro  Arg  Gly  Thr  His  Phe  Arg  Arg
               20                     25                     30

GCA  GGA  CCA  CGT  CAA  AGG  GTT  TAC  TTT  GAT  TCG  GAT  GAT  GTT  GTT  GCG    144
Ala  Gly  Pro  Arg  Gln  Arg  Val  Tyr  Phe  Asp  Ser  Asp  Asp  Val  Val  Ala
          35                     40                     45

TGC  ATT  GTT  ACA  TGT  GGT  GGC  TTG  TGT  CCA  GGG  CTT  AAT  ACT  GTC  ATC    192
Cys  Ile  Val  Thr  Cys  Gly  Gly  Leu  Cys  Pro  Gly  Leu  Asn  Thr  Val  Ile
     50                     55                     60

AGA  GAA  ATC  GTT  TGT  GGA  TTG  TCT  TAC  ATG  TAT  GGT  GTC  AAG  AAA  ATC    240
Arg  Glu  Ile  Val  Cys  Gly  Leu  Ser  Tyr  Met  Tyr  Gly  Val  Lys  Lys  Ile
65                     70                     75                     80

CTT  GGC  ATT  GAG  GGA  GGT  TAC  AGA  GGC  TTC  TAC  GCT  AGG  AAC  ACG  ATC    288
Leu  Gly  Ile  Glu  Gly  Gly  Tyr  Arg  Gly  Phe  Tyr  Ala  Arg  Asn  Thr  Ile
               85                     90                     95
```

| | | | | | | | | | | | | | | | | |
|---|---|---|---|---|---|---|---|---|---|---|---|---|---|---|---|---|
| GAT | TTG | GAT | TTG | AAA | ACA | GTG | AAT | GAT | ATT | CAT | AAA | CGT | GGA | GGA | ACC | 336 |
| Asp | Leu | Asp | Leu | Lys | Thr | Val | Asn | Asp | Ile | His | Lys | Arg | Gly | Gly | Thr | |
| | | | 100 | | | | 105 | | | | | 110 | | | | |
| ATC | CTC | GGG | ACT | TCA | AGA | GGT | GGT | CAC | GAC | ACT | ACT | AAG | ATA | GTT | GAT | 384 |
| Ile | Leu | Gly | Thr | Ser | Arg | Gly | Gly | His | Asp | Thr | Thr | Lys | Ile | Val | Asp | |
| | | 115 | | | | | 120 | | | | | 125 | | | | |
| AGT | ATT | CAA | GAT | CGT | GGG | ATT | AAC | CAG | GTT | TAT | ATA | ATC | GGT | GGA | GAT | 432 |
| Ser | Ile | Gln | Asp | Arg | Gly | Ile | Asn | Gln | Val | Tyr | Ile | Ile | Gly | Gly | Asp | |
| | 130 | | | | | 135 | | | | | 140 | | | | | |
| GGA | TCA | CAG | AAA | GGA | GCA | GCT | GTT | ATA | TTC | GAG | GAG | ATT | AGG | AGA | CGT | 480 |
| Gly | Ser | Gln | Lys | Gly | Ala | Ala | Val | Ile | Phe | Glu | Glu | Ile | Arg | Arg | Arg | |
| 145 | | | | | 150 | | | | | 155 | | | | | 160 | |
| GGA | CTC | AAA | GTT | GCT | GTT | GCA | GGG | ATC | CCC | AAA | ACA | ATC | GAC | AAT | GAC | 528 |
| Gly | Leu | Lys | Val | Ala | Val | Ala | Gly | Ile | Pro | Lys | Thr | Ile | Asp | Asn | Asp | |
| | | | | 165 | | | | | 170 | | | | | 175 | | |
| ATT | CCT | ATT | ATC | GAT | AGA | TCG | TTC | GGG | TTT | GAC | ACA | GCT | GTA | GAA | GAG | 576 |
| Ile | Pro | Ile | Ile | Asp | Arg | Ser | Phe | Gly | Phe | Asp | Thr | Ala | Val | Glu | Glu | |
| | | | 180 | | | | | 185 | | | | | 190 | | | |
| GCT | CAA | CGT | GCT | ATC | AAC | GCA | GCT | CAT | GTG | GAA | GCT | ACA | AGT | TTT | GAG | 624 |
| Ala | Gln | Arg | Ala | Ile | Asn | Ala | Ala | His | Val | Glu | Ala | Thr | Ser | Phe | Glu | |
| | | 195 | | | | | 200 | | | | | 205 | | | | |
| AAT | GGT | ATT | GGT | CTT | GTC | AAG | TTA | ATG | GGA | CGT | TAT | AGT | GGA | TTC | ATT | 672 |
| Asn | Gly | Ile | Gly | Leu | Val | Lys | Leu | Met | Gly | Arg | Tyr | Ser | Gly | Phe | Ile | |
| | 210 | | | | | 215 | | | | | 220 | | | | | |
| GCG | ATG | TAT | GCA | ACA | CTA | GCC | AGC | AGA | GAC | GTG | GAC | TGC | TGC | TTG | ATC | 720 |
| Ala | Met | Tyr | Ala | Thr | Leu | Ala | Ser | Arg | Asp | Val | Asp | Cys | Cys | Leu | Ile | |
| 225 | | | | | 230 | | | | | 235 | | | | | 240 | |
| CCG | GAA | TCT | CCA | TTT | TTT | CTT | GAA | GGC | AAA | GGC | GGT | CTT | TTC | GAG | TTT | 768 |
| Pro | Glu | Ser | Pro | Phe | Phe | Leu | Glu | Gly | Lys | Gly | Gly | Leu | Phe | Glu | Phe | |
| | | | | 245 | | | | | 250 | | | | | 255 | | |
| ATC | GGT | AAA | CGG | CTA | AAG | GAG | ATT | GGT | CAC | ATG | GTG | ATT | GTG | ATA | GCA | 816 |
| Ile | Gly | Lys | Arg | Leu | Lys | Glu | Ile | Gly | His | Met | Val | Ile | Val | Ile | Ala | |
| | | | 260 | | | | | 265 | | | | | 270 | | | |
| GAA | GGT | GCT | GGA | CAA | GAT | CTG | TTG | GCT | GAA | AGC | AAT | GAA | CAG | TCC | ACA | 864 |
| Glu | Gly | Ala | Gly | Gln | Asp | Leu | Leu | Ala | Glu | Ser | Asn | Glu | Gln | Ser | Thr | |
| | | 275 | | | | | 280 | | | | | 285 | | | | |
| ACC | CTC | AAA | GAT | GCA | TCT | GGG | AAC | AAA | CTT | CTA | CAA | GAC | GTT | GGC | CTA | 912 |
| Thr | Leu | Lys | Asp | Ala | Ser | Gly | Asn | Lys | Leu | Leu | Gln | Asp | Val | Gly | Leu | |
| | 290 | | | | | 295 | | | | | 300 | | | | | |
| TGG | ATC | TCC | CAA | CGG | ATC | AAG | GAT | CAT | TTT | GCC | AAG | AAG | ATG | ACC | CTA | 960 |
| Trp | Ile | Ser | Gln | Arg | Ile | Lys | Asp | His | Phe | Ala | Lys | Lys | Met | Thr | Leu | |
| 305 | | | | | 310 | | | | | 315 | | | | | 320 | |
| AAC | CTG | AAA | TAC | ATA | GAT | CCA | ACC | TAC | ATG | ATA | AGG | GCT | GTT | CCG | AGC | 1008 |
| Asn | Leu | Lys | Tyr | Ile | Asp | Pro | Thr | Tyr | Met | Ile | Arg | Ala | Val | Pro | Ser | |
| | | | | 325 | | | | | 330 | | | | | 335 | | |
| AAT | GCA | TCA | GAC | AAT | GTA | TGC | TGC | ACG | CTG | TTA | GCT | CAA | AGC | GCG | GTT | 1056 |
| Asn | Ala | Ser | Asp | Asn | Val | Cys | Cys | Thr | Leu | Leu | Ala | Gln | Ser | Ala | Val | |
| | | | 340 | | | | | 345 | | | | | 350 | | | |
| CAT | GGA | GTG | ATG | GCT | GGT | TAC | AAT | GGC | TTC | ACC | GTT | GGT | CTT | GTT | AAT | 1104 |
| His | Gly | Val | Met | Ala | Gly | Tyr | Asn | Gly | Phe | Thr | Val | Gly | Leu | Val | Asn | |
| | | 355 | | | | | 360 | | | | | 365 | | | | |
| GGC | AGA | CAT | ACT | TAC | ATT | CCC | TTC | TAT | AGG | ATC | ACT | GAG | AAA | CAG | AAC | 1152 |
| Gly | Arg | His | Thr | Tyr | Ile | Pro | Phe | Tyr | Arg | Ile | Thr | Glu | Lys | Gln | Asn | |
| | 370 | | | | | 375 | | | | | 380 | | | | | |
| AAG | GTG | GTG | ATC | ACT | GAC | AGA | ATG | TGG | GCA | AGG | CTT | TTG | TCT | TCG | ACA | 1200 |
| Lys | Val | Val | Ile | Thr | Asp | Arg | Met | Trp | Ala | Arg | Leu | Leu | Ser | Ser | Thr | |
| 385 | | | | | 390 | | | | | 395 | | | | | 400 | |
| AAC | CAG | CCT | AGT | TTC | ATG | AAG | CAC | GAT | GAT | CAC | CAC | GAG | CCA | AAC | CAT | 1248 |
| Asn | Gln | Pro | Ser | Phe | Met | Lys | His | Asp | Asp | His | His | Glu | Pro | Asn | His | |
| | | | | 405 | | | | | 410 | | | | | 415 | | |

```
TCT GGT GGT GAA GCA GGT GCC ATG AAC TGG TGAAACAACT CTTGTCTGAC        1298
Ser Gly Gly Glu Ala Gly Ala Met Asn Trp
            420                 425

AATCATTTTG TTTGAGAAAG AAAGTAAGGT TTCTTTATTT TGATAGAAGC TTCTCAAAAT    1358

GTTTTATAAA TCTTTCTTCA AGCAAAAGAG AAAGAGAGAG ATATACATTT CCTCCTTGGA    1418

GAAGTTCATA CAGTTATAAT TGTGATAAAT CCATGTATTA AACTTTGGAG AGTGATCTTG    1478

CACTTGCCAA ACTGTAATTT ACACTTTTAT AATAACAAAT CTATAAGGAA ATGTTTGGT    1538

TCAAAAAAAA AAAAAAAAA                                                 1558
```

( 2 ) INFORMATION FOR SEQ ID NO:10:

( i ) SEQUENCE CHARACTERISTICS:
        ( A ) LENGTH: 426 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser Val Val Lys Gln Tyr Phe Val Asp Glu Asp Thr Val Pro Gln
 1           5                  10                  15

Lys Ile Val Val His Pro Asp Ser Pro Arg Gly Thr His Phe Arg Arg
             20                  25                  30

Ala Gly Pro Arg Gln Arg Val Tyr Phe Asp Ser Asp Val Val Ala
             35                  40                  45

Cys Ile Val Thr Cys Gly Gly Leu Cys Pro Gly Leu Asn Thr Val Ile
     50                  55                  60

Arg Glu Ile Val Cys Gly Leu Ser Tyr Met Tyr Gly Val Lys Lys Ile
65                   70                  75                  80

Leu Gly Ile Glu Gly Gly Tyr Arg Gly Phe Tyr Ala Arg Asn Thr Ile
                 85                  90                  95

Asp Leu Asp Leu Lys Thr Val Asn Asp Ile His Lys Arg Gly Gly Thr
                100                 105                 110

Ile Leu Gly Thr Ser Arg Gly Gly His Asp Thr Thr Lys Ile Val Asp
            115                 120                 125

Ser Ile Gln Asp Arg Gly Ile Asn Gln Val Tyr Ile Ile Gly Gly Asp
130                 135                 140

Gly Ser Gln Lys Gly Ala Ala Val Ile Phe Glu Glu Ile Arg Arg Arg
145                 150                 155                 160

Gly Leu Lys Val Ala Val Ala Gly Ile Pro Lys Thr Ile Asp Asn Asp
                165                 170                 175

Ile Pro Ile Ile Asp Arg Ser Phe Gly Phe Asp Thr Ala Val Glu Glu
                180                 185                 190

Ala Gln Arg Ala Ile Asn Ala Ala His Val Glu Ala Thr Ser Phe Glu
            195                 200                 205

Asn Gly Ile Gly Leu Val Lys Leu Met Gly Arg Tyr Ser Gly Phe Ile
210                 215                 220

Ala Met Tyr Ala Thr Leu Ala Ser Arg Asp Val Asp Cys Cys Leu Ile
225                 230                 235                 240

Pro Glu Ser Pro Phe Phe Leu Glu Gly Lys Gly Gly Leu Phe Glu Phe
                245                 250                 255

Ile Gly Lys Arg Leu Lys Glu Ile Gly His Met Val Ile Val Ile Ala
            260                 265                 270

Glu Gly Ala Gly Gln Asp Leu Leu Ala Glu Ser Asn Glu Gln Ser Thr
            275                 280                 285
```

```
Thr  Leu  Lys  Asp  Ala  Ser  Gly  Asn  Lys  Leu  Leu  Gln  Asp  Val  Gly  Leu
     290                      295                     300

Trp  Ile  Ser  Gln  Arg  Ile  Lys  Asp  His  Phe  Ala  Lys  Lys  Met  Thr  Leu
305                      310                     315                      320

Asn  Leu  Lys  Tyr  Ile  Asp  Pro  Thr  Tyr  Met  Ile  Arg  Ala  Val  Pro  Ser
                    325                     330                      335

Asn  Ala  Ser  Asp  Asn  Val  Cys  Cys  Thr  Leu  Leu  Ala  Gln  Ser  Ala  Val
               340                      345                      350

His  Gly  Val  Met  Ala  Gly  Tyr  Asn  Gly  Phe  Thr  Val  Gly  Leu  Val  Asn
          355                      360                      365

Gly  Arg  His  Thr  Tyr  Ile  Pro  Phe  Tyr  Arg  Ile  Thr  Glu  Lys  Gln  Asn
     370                      375                     380

Lys  Val  Val  Ile  Thr  Asp  Arg  Met  Trp  Ala  Arg  Leu  Leu  Ser  Ser  Thr
385                      390                     395                      400

Asn  Gln  Pro  Ser  Phe  Met  Lys  His  Asp  Asp  His  His  Glu  Pro  Asn  His
                    405                     410                      415

Ser  Gly  Gly  Glu  Ala  Gly  Ala  Met  Asn  Trp
                    420                     425
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Arg  Ala  Gly  Pro  Arg
1                    5
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Ile  Val  Thr  Cys  Gly  Gly  Leu  Cys  Pro  Gly  Leu  Asn
1                   5                     10
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Gly  Tyr  Arg  Gly  Phe  Tyr
1                    5
```

( 2 ) INFORMATION FOR SEQ ID NO:14:

( i ) SEQUENCE CHARACTERISTICS:
        ( A ) LENGTH: 6 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ile  Val  Asp  Ser  Ile  Gln
    1                  5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Pro  Lys  Thr  Ile  Asp  Asn  Asp  Ile
    1                  5

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Phe  Gly  Phe  Asp  Thr  Ala  Val  Glu
    1                  5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Ala  Gln  Arg  Ala  Ile  Asn
    1                  5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Val  Lys  Leu  Met  Gly  Arg
    1                  5

(2) INFORMATION FOR SEQ ID NO:19:

(i) SEQUENCE CHARACTERISTICS:
        (A) LENGTH: 5 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:19:

Ser Gly Phe Ile Ala
1               5

(2) INFORMATION FOR SEQ ID NO:20:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:20:

Ala Glu Gly Ala Gly Gln
1               5

(2) INFORMATION FOR SEQ ID NO:21:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:21:

Asp Ala Ser Gly Asn
1               5

(2) INFORMATION FOR SEQ ID NO:22:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:22:

Leu Lys Tyr Ile Asp Pro Thr Tyr Met
1               5

(2) INFORMATION FOR SEQ ID NO:23:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:23:

Cys Leu Ile Pro Glu
1               5

DNA ENCODING ATP-DEPENDENT FRUCTOSE 6-PHOSPHATE 1-PHOSPHOTRANSFERASE ORIGINATING FROM PLANT, RECOMBINANT VECTOR CONTAINING THE SAME AND METHOD FOR CHANGING SUGAR CONTENT IN PLANT CELLS UNDER LOW TEMPERATURE

TECHNICAL FIELD

This invention relates to a DNA encoding ATP-dependent fructose 6-phosphate 1-phosphotransferase (EC 2.7.1.11) (hereinafter referred to as "PFK"), a recombinant vector containing the same and a method for changing sugar content in plant cells under low temperature using the recombinant vector.

BACKGROUND ART

PFK is an enzyme which catalyzes the phosphorylation of fructose 6-phosphate (F6P) to fructose 1,6-bisphosphate, a key regulatory step in the glycolytic pathway.

It is well-known that when plant tissues are exposed to a low temperature, the content of sugars such as sucrose, glucose, fructose and the like is generally increased. For example, this phenomenon is observed in potato tubers. Accumulation of reducing sugars such as glucose and fructose in potato tubers during storage at low temperature is undesirable in industry because they cause excess browning of potato chips during processing. As for the cause of the accumulation of the reducing sugars, there are various hypotheses. However, it is thought that the activity of the glycolytic pathway is greatly reduced at low temperatures, so that the flow of the breakdown products of starch to sucrose is increased, thereby increasing the accumulation of the reducing sugars. PFK is thought to be one of the key enzymes of the glycolytic pathway, and it is well-known that PFK is cold labile. Therefore, it is thought that the drastic reduction of the activity of the glycolytic pathway at low temperature is caused by the drastic reduction of the activity of PFK.

PFK genes have been isolated from prokaryotes such as *Escherichia coli*, thermophilic bacteria, *Bacillus subtilis* and mycoplasma, and from eukaryotic tissues such as human muscle, human liver, rabbit muscle and mouse liver. However, the isolation of a plant PFK gene has not been reported, and the isolation of a gene encoding cold stable PFK has also not been reported. Therefore, it has been difficult hitherto to develop a potato variety resistant to Cold Induced Sweetening by introducing PFK genes. Nor has it been possible to reduce the activity of the glycolytic pathway in plant tissues by expressing an anti-sense PFK gene, thereby developing a plant having a high sugar content, which has a new taste.

European Patent Publication 0 438 904 (Japanese Laid-open Patent Application (Kokai) No. 4-341126) discloses an example of introducing a PFK gene into a plant. In the invention described in this publication, the *E. coli* PFK gene is expressed in potato and rice and it is shown that the amount of several intermediates of the pathways of the carbohydrate metabolism are changed. In particular, it is shown that the sucrose content in the tubers immediately after harvest is significantly decreased. However, in the invention of the publication, the amount of glucose and fructose in the tubers during storage at low temperature, which is an industrial problem, is not mentioned. In view of the fact that *E. coli* PFK is an enzyme which is cold labile (Kruger, N. J. (1989) Biochemical Society Transaction 629th Meeting, London Vol. 17, 760–761), it is expected that a potato variety resistant to Cold Induced Sweetening cannot be obtained by introducing the *E. coli* PFK gene into potato and expressing it in the tubers. To attain this objective, a gene encoding PFK which is cold stable is necessary. However, a gene for a cold stable PFK has not yet been isolated.

In order to store potato tubers for a long time, storage at low temperature after harvest is very important for suppressing diseases, sprouting and aging.

However, when tubers stored at low temperature are directly used to make potato chips or French fries, browning of the products occurs during processing and the product values are greatly decreased (especially in potato chips). It is known that this browning is caused by the Maillard reaction between amino acids and reducing sugars contained in potato tubers, which occurs during processing in a hot cooking oil (Schallenberger, R. S. et al., (1959) J. Agric. Fd Chem., 7, 274). It is known that the amount of the reducing sugars (glucose and fructose) in the tubers is increased when the tubers are stored at a low temperature, and a high correlation is observed between the amount of glucose and fructose in the tubers and the degree of browning. Thus, it is thought that the increase in the amount of glucose and fructose during storage at a low temperature is the main cause of browning in the processing of the potato (Gray, D. and Hughes, J. C. (1978) The Potato Crop (ed. P. M. Harris), Chapman & Hall, London, pp.504–544).

At present, processors of potato chips use tubers stored at a low temperature of about 8° C. (the temperature varies depending on the varieties) and treatment with a sprout suppressant. However, reducing sugars accumulate to an unacceptable degree, so that they use the potato tubers after decreasing the amount of the reducing sugars by treatments called blanching or reconditioning before the processing. Since these treatments are costly and troublesome, if a new variety of potato were developed, in which the reducing sugars did not accumulate at the storage temperature currently employed, the cost of processing would be decreased. Further, if a variety of potato were developed, in which the reducing sugars hardly accumulated at a temperature as low as 2°–4° C., not only the labor and cost for the pretreatments such as blanching and reconditioning can be saved, but also germination, which is the cause of aging and loss of dry weight, can be avoided, so that long-term storage without using a sprout suppressant can be possible. Residues of such chemicals in tubers are problematic from the point of view of health hazards. Thus, development of a potato variety resistant to Cold Induced Sweetening is strongly desired by the processors.

Although the mechanism of the accumulation of glucose and fructose during storage at low temperature is complicated and involves various physiological changes in the tubers, it is thought that one of the major causes is the drastic reduction in the activity of PFK at low temperature. PFK is said to be a key regulatory enzyme of the glycolytic pathway (Dixon, W. L. and ap Rees, T. (1980) Phytochem., 19, 1653; Dixon, W. L. et al., (1981) Phytochem., 20, 969; Pollock, C. J. and ap Rees, T. (1975) Phytochem., 14, 613). In tubers during storage at low temperature, it is thought that reducing sugars are supplied by breakdown products of starch through F6P. The biological reactions using F6P as a substrate are roughly divided into two. One is the reaction catalyzed by PFK, by which F6P enters the glycolytic pathway, and the other is the reaction catalyzed by sucrose-6-phosphate synthase (hereinafter referred to as "SPS", EC 2.4.1.14), by which F6P enters the sucrose synthesis pathway. Thus, these two enzymes compete for F6P. In potato tubers stored at room temperature after harvest, the amount of glucose and fructose that accumulate is usually very small as long as sprouting and aging do not occur. It is thought that this is because of higher PFK activity than SPS activity, so that F6P preferentially enters the glycolytic pathway. However, at low temperature, the enzyme activity of PFK is drastically decreased and SPS activity is higher than PFK activity, so that F6P preferentially flows into the sucrose synthesis pathway rather than into the glycolytic pathway. The sucrose is finally converted to glucose and fructose by invertase (EC 3.2.1.26) and glucose and fructose accumulate. Thus, the decrease in the activity of the glycolytic pathway due to the decrease in PFK activity is thought to be a cause of the increase in the amount of glucose and fructose in potato tubers during storage at low temperature. This hypothesis was supported by Hammond et al (Planta 180, 613–616, 1990) who reported that cold stable PFKs exist in the tubers of a variety resistant to Cold Induced Sweetening, whereas PFKs are not cold stable in the usual processing variety in which the reducing sugar content increases during storage at low temperature. Thus, it is suggested that the stability of PFK to low temperature in the tubers is the main factor which determines the amount of glucose and fructose during storage at low temperatures.

If a DNA encoding cold stable PFK is obtained, the activity of the glycolytic pathway in the tubers during storage at low temperature can be promoted by introducing the DNA into potato, so that a potato maintaining low amounts of sugars under low temperature in tubers can be developed. In this way, processors can save the cost of blanching and reconditioning currently carried out for decreasing the content of reducing sugars.

SUMMARY OF THE INVENTION

Accordingly, an object of the present invention is to provide a DNA encoding a cold stable PFK. Another object of the present invention is to provide a recombinant vector which expresses the cold stable PFK in a host cell. Still another object of the present invention is to provide a method for changing the sugar content in plant cells under low temperature by transforming the plant with the recombinant vector.

To attain the above-described objects, the present inventors tried to isolate and analyze a cDNA (containing coding region and non-coding region) encoding one of the isozymes of PFK originating from a plant tissue having cold stable PFK, particularly from tubers of potato variety Brodick, and succeeded in accomplishing this. Further, it was confirmed that the isolated gene expresses cold stable PFK in E. coli and in potato tubers, and that the glucose content in tubers of the potato in which the gene is expressed and which were stored at a low temperature is decreased and so the color of the potato chips produced from the tubers is improved. Further, the inventors succeeded in isolating PFK genes of various plants using the potato PFK gene as a probe, and hence identified amino acid sequences which are specific to and commonly contained in various plant PFKs.

That is, the present invention provides a DNA encoding PFK originating from a plant. The present invention also provides a recombinant vector comprising the DNA according to the present invention, which can express PFK originating from a plant in a host cell. The present invention still further provides a method for changing the sugar content in plant cells under low temperature, which comprises transforming said plant with said recombinant vector. The present invention further provides DNAs encoding the amino acid sequences identified as Sequence ID Nos. 11, 14, 21 and 22 in the Sequence Listing. The present invention still further provides a method for detecting a plant PFK gene by hybridizing sample DNAs with the DNA identified as Sequence ID Nos. 11–22 in the Sequence Listing or a part thereof, or a DNA containing said DNA identified as Sequence ID Nos. 11–22. The present invention still further provides a method for amplifying a plant PFK gene by the polymerase chain reaction (PCR) by using as a primer the DNA identified as Sequence ID Nos. 11–22 or a part thereof, or a DNA containing said DNA identified as Sequence ID Nos. 11–22.

By the present invention, a DNA encoding a cold stable PFK and a recombinant vector containing the same were first provided. By introducing the recombinant vector according to the present invention to a plant and expressing the same in the plant by a genetic engineering method, the glucose content in tuber tissue stored at a low temperature can be decreased when compared with tubers of non-transformed plants. Therefore, the present invention can be used for developing a potato resistant to Cold Induced Sweetening. Further, since the DNA according to the present invention originated from a plant, it can be used for the isolation of other plant PFK genes, whereas the PFKs of other organisms are difficult to use as probes for the isolation of plant PFKs. Further, if various plant PFK genes are isolated, the PFK activity in plant cells can be reduced by antisense RNAs. Thus, for example, glycolysis can be modified, or respiration can be reduced, so that sweet fruits and vegetables containing more sugar can be prepared.

DETAILED DESCRIPTION OF THE INVENTION

Figure 1:
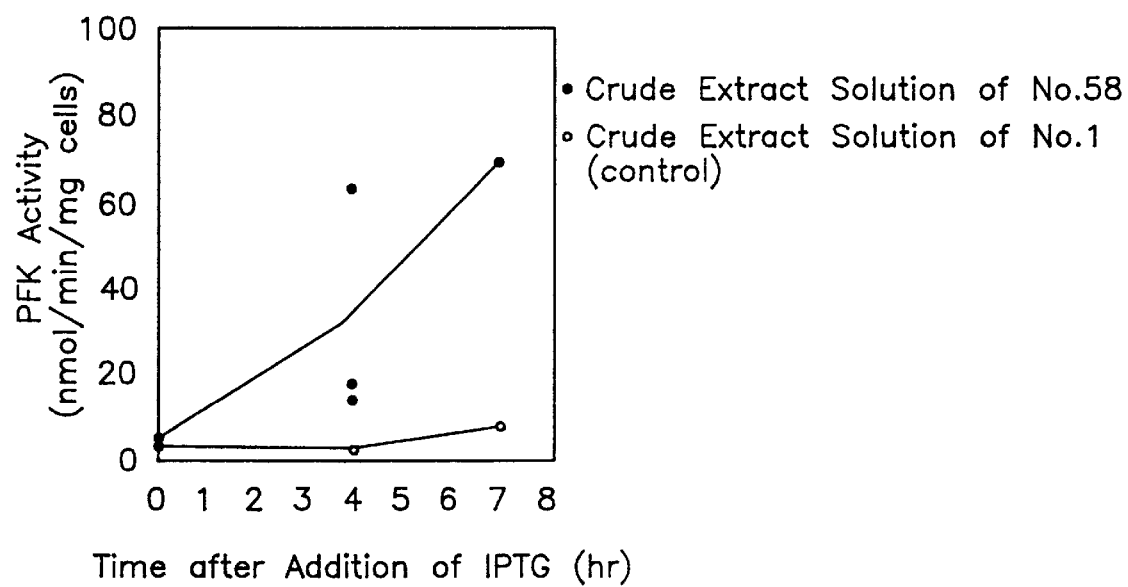
FIG. 1 shows the induction of the PFK activity with time in E. coli No. 58 transformed with the recombinant vector of the present invention and of a control E. coli No. 1, after adding IPTG.

As described above, the DNA according to the present invention encodes a plant PFK. The DNAs encoding PFKs of potato (Solanum tuberosum L.), flaveria (Flaveria brownii), rice (Oryza sativa), maize (Zea mays) and radish (Raphanus sativus), which are examples of the DNA of the present invention, encode the amino acid sequences identified as Sequence ID Nos. 2, 4, 6, 8 and 10 in the Sequence Listing described below, respectively. Examples of such DNAs are the DNAs identified as Sequence ID Nos. 1, 3, 5, 7 and 9 in the Sequence Listing, which were actually cloned and the DNA sequences were actually determined in the examples described below. However, the DNA according to the present invention is not limited thereto (It should be noted that the amino acid sequences of Sequence ID Nos. 2, 4, 6, 8 and 10 are the same as the amino acid sequences shown in Sequence ID Nos. 1, 3, 5, 7 and 9, respectively). In particular, although the DNA having the DNA sequence shown in Sequence ID Nos. 1, 3, 5, 7 and 9 are cDNAs, since the amino acid sequences of plant PFKs and the DNA sequences encoding the PFKs were determined by the present invention, the genomic DNA encoding the amino acid sequences identified as Sequence ID Nos. 2, 4, 6, 8 and 10 can be easily prepared by the PCR method using the genomic DNA as a template. Therefore, it is construed that such genomic DNAs (which may contain introns) are within the scope of the present invention.

The plant PFK encoded by the above-described DNA coding for the amino acid sequence identified as Sequence ID No. 2 or by the above-described DNA having the DNA sequence shown in Sequence ID No. 1 has a Q10 value (described below) at 5° C. of not more than 2.4 as described concretely in the examples below. If the Q10 value of a PFK is not more than 2.4 at 5° C., it can be said that the PFK is cold stable.

The DNA according to the present invention may be obtained by, for example, the following method.

Firstly, to isolate poly(A)$^+$ RNA corresponding to PFK from a plant tissue, it is preferred to isolate the total RNAs which have not been decomposed. The preferred starting material is a plant tissue which is known to contain cold stable PFK, such as potato variety Brodick (which is resistant to Cold Induced Sweetening).

The total RNAs may be isolated from potato tubers by, for example, sodium dodecyl sulfate (SDS)/phenol method. PFK poly(A)$^+$ RNA may be obtained from the total RNAs by using Dynabeads mRNA purification kit (DYNAL). Since it is not easy to directly isolate the PFK poly(A)$^+$ RNA by this treatment, it is preferred to prepare cDNAs using the obtained poly(A)$^+$ RNAs as templates and to prepare a cDNA library containing the cDNAs. More particularly, a cDNA library may be prepared by synthesizing double-stranded cDNAs by the method of Gubler and Hoffman (Gene, 25:263, 1983) or the like, ligating the cDNAs to appropriate vectors via an adaptor DNA by a DNA ligase, and by transforming the host microorganisms with the thus prepared vectors. In cases where the host microorganism is E. coli, it is preferred to use a vector of the pUC series or A phage series. Double-stranded cDNAs, prepared from poly (A)$^+$ RNAs from tubers of potato variety Brodick, may be inserted using a DNA ligase into the Eco RI site of λgt10 phage vector via an adaptor DNA containing Eco RI and Not I sites. Phage particles may then be prepared, thereby obtaining a cDNA library. A cDNA clone corresponding to the PFK poly(A)$^+$ RNA is then identified in the thus prepared cDNA library.

The identification of a PFK cDNA clone may be carried out by the plaque hybridization method using synthesized oligonucleotides based on the partially determined amino acid sequence of the purified plant PFK, or a DNA having a part of the DNA sequence of the PFK gene, which may be amplified by the polymerase chain reaction (PCR) using the above-mentioned oligonucleotides as primers and using the plant genomic DNA or cDNA as a template.

Then the transformants containing the DNA encoding the PFK originated from potato tubers are cultured in a large scale by the plate lysate method or the like. The desired phage DNA is then purified by a conventional method such as Sambrook's method (Molecular Cloning: A laboratory Manual/Second Edition, Cold Spring Harbor Laboratory Press, 1989). The purified phage DNA is then digested with restriction enzyme Not I and subjected to agarose gel electrophoresis or the like to obtain the cDNA encoding PFK. Further, once the potato PFK gene is isolated, PFK genes can easily be isolated from various plants using the isolated potato PFK gene or a part thereof as a probe or using a part thereof as a primer for conducting PCR.

As described in examples below, cDNAs of PFK genes of various plants were cloned and their nucleotide sequences and amino acid sequences deduced therefrom were determined. By comparing the amino acid sequences of the various plants, 13 amino acid sequences having not less than 5 amino acid residues, which are common in plant PFKs, were identified. Therefore, PFK genes of various plants can be detected or amplified using oligonucleotides encoding these sequences or a part thereof, or nucleotides containing the region encoding these sequences, as a probe or a primer for PCR. The DNAs encoding the amino acid sequences shown in Table 7 can be easily synthesized chemically. Among these, sequences (1), (4), (11) and (12) in Table 7 (i.e., Sequence ID Nos. 11, 14, 21 and 22) are common in PFKs of plants but not found in PFKs of organisms other than plants. Thus, these are specific for plants. Therefore, by utilizing these sequences, plant PFKs can be detected or amplified avoiding the possible contamination by PFK from other organisms. As probes, oligonucleotides of at least 15 bases up to the full length of the gene are preferred. Methods for labelling the oligonucleotides with a radioactive marker, a fluorescent marker or the like are well-known in the art. As primers for PCR, oligonucleotides of 15–30 bases are preferred.

The PFK cDNA thus obtained may be used for transforming microorganisms, plants and animals after preparing a recombinant vector with a vector for microorganisms, plants or animals, thereby increasing the PFK activity in the transformed microorganism, plant or animal tissue. The PFK cDNA may also be used for inhibiting the intrinsic PFK activity of a plant by inserting the PFK cDNA in a reverse direction in a vector and expressing the cDNA in a plant tissue such as potato tuber.

Examples of the microorganisms include bacteria belonging to the genus Escherichia such as E. coli and yeasts belonging to the genus Saccharomyces such as baker's yeast. Examples of the plants include dicotyledons which can be transformed by Agrobacterium-Ri/Ti plasmid system, such as those belonging to the family Solanaceae such as potato, tobacco, and tomato; those belonging to the family Cucurbitaceae such as melon and cucumber; those belonging to the family Cruciferae such as radish and rapeseed; and fruits such as grape and oranges. Examples of the plants which can be transformed by PEG-calcium phosphate method, electroporation method, particle bombardment method or the like include monocotyledons such as those belonging to the family Gramineae represented by rice, corn and the like. Examples of the animals include various cultured cells (e.g., BALB/c-3T9 and the like) of human, mouse and the like. The vectors which may be used for these hosts will now be exemplified below.

Examples of the vectors for bacteria include various plasmid vectors (e.g., pBR322, pUC series vectors and the like) and phage vectors (e.g., λgt10, λgt11, λZAP and the like) which are described in references (e.g., Molecular Cloning: A Laboratory Manual/Second Edition, Cold Spring Harbor Laboratory Press, 1989). Examples of the vectors for yeast and animal cells include those described in references (e.g., Molecular Cloning: A Laboratory Manual/Second Edition, Cold Spring Harbor Laboratory Press, 1989). Examples of the vectors for plants include various plasmid vectors and those originated from Ti plasmid such as binary vectors (e.g., pGA482, pBin19 and the like) (An G. et al., (1986) Plant Physiol. 81, 301; Bevan, M., (1984) Nucleic Acids Research 12, 8711). In cases where a plant vector originated from Ti plasmid is used, the obtained recombinant DNA is introduced into a bacterium belonging to the genus Agrobacterium such as *Agrobacterium tumefaciens* (e.g., LBA4404), and the resulting transformed bacterium is infected to a plant tissue or callus by, for example, culturing the tissue or callus with the bacterium, thereby introducing the cDNA to the host plant (Komari, T. (1989) Plant Science, 60, 223: Visser, R. G. F. et al., (1989) Plant Molecular Biology 12, 329, etc). Plant individuals containing the recombinant DNA may be obtained by regenerating an organ or whole plant by a known tissue culture method.

(Millipore) and stained with CBB. The stained band was cut out together with the PVDF membrane using a razor blade and the obtained band was subjected to determination of the amino acid sequence of the N-terminal region. For determining the amino acid sequence of the N-terminal region of the purified PFK, the above-described final purified PFK sample was used as it is. The analysis was carried out by the solid phase or gas phase sequencing method (This analysis was entrusted to The Department of Biochemistry, Leeds University and The Department of Biochemistry, University of Cambridge). From both samples, the amino acid sequence of the N-terminal region of the purified PFK was determined, which is shown in Table 1. The determined amino acid sequence was compared with amino acid sequences of known proteins by using a database (The Swiss Prot data bank (Release 23)), but no amino acid sequences having a significant homology were found.

TABLE 1

Determined N-terminal Amino Acid Sequence of PFK from Potato Tubers

| Thr | Glu | Ser | Asn | Tyr | Gln | Met | Lys | Val | Val | Lys | Gly | Asp | Tyr | Gly | Tyr | Val | Leu | Glu | Asp | Val | ? | ? | Leu |
|-----|-----|-----|-----|-----|-----|-----|-----|-----|-----|-----|-----|-----|-----|-----|-----|-----|-----|-----|-----|-----|---|---|-----|
|     |     |     |     |     |     |     | Val |     |     | Glu |     |     |     |     |     |     |     |     |     | Asp |   |   |     |
|     |     |     |     |     |     |     | Ala |     |     |     |     |     |     |     |     |     |     |     |     |     |   |   |     |

EXAMPLES

The present invention will now be described more concretely by way of examples. It should be noted that the present invention is not restricted to the following examples.

1: Purification of Potato PFK

PFK was purified from 5 kg of tubers of potato variety Record or Maris Piper by a modification of the method of Kruger et al (Arch. Bioichem. Biophys. 267, 690–700, 1988), in which PFK was fractionated and purified by sodium dodecyl sulfate polyacrylamide gel (containing 4M urea) electrophoresis (SDS-PAGE) rather than by Mono Q column chromatography, after the ATP agarose column chromatography. More particularly, the fraction containing PFK activity was concentrated to about 0.5 ml by ultrafiltration and equivolume of a sample buffer (62.5 mM Tris-HCl (pH 6.8), 2% SDS, 5% 2-mercaptoethanol, 10% glycerol, 4M urea, 0.001% Bromphenol Blue) was added. The resulting mixture was heated at 65° C. for 10 minutes and the resultant was subjected to electrophoresis. The composition of the gel was the same as that employed in the method of Kruger et al (Arch. Bioichem. Biophys. 267, 690–700, 1988). After the electrophoresis, the gel was stained with Coomassie Briliant Blue R-250 (CBB) and the portion of the gel containing the PFK polypeptide having a molecular weight of about 53 kDa was cut out with a razor blade. The polypeptide was eluted from the gel by using an electroelution apparatus (Model 422 Electroeluter, commercially available from BIO-RAD), and the resultant was dialyzed against a solution containing 50 mM ammonium bicarbonate and 0.001% SDS, followed by drying under vacuum to obtain a final purified sample.

2: Determination of Amino Acid Sequence of Potato PFK

The purified PFK sample was digested with V8 protease (originated from *Staphylococcus aureus*) in accordance with the method of Kruger et al (Arch. Bioichem. Biophys. 267, 690–700, 1988), and the digestion product was fractionated by SDS-PAGE according to the method of Kruger et al (Arch. Bioichem. Biophys. 267, 690–700, 1988). The fractionated polypeptides were transferred to a PVDF membrane 3. Synthesis of DNA Encoding Determined Amino Acid Sequence of Potato PFK Based on the determined amino acid sequence, the oligonucleotides having the base sequences shown in Table 2 were prepared by a DNA synthesizer (Applied Biosystems) according to the manual of the synthesizer, and the synthesized oligonucleotides were used as primers of PCR described below.

TABLE 2

DNA Primers Synthesized Based on Determined Amino Acid Sequence

| Primer Name | DNA sequence (5' → 3') | Degeneracy |
|-------------|------------------------|------------|
| N10:        | ACGGAAAGTAATTATCAAATG<br>  A   GTC   C    C    G<br>  T<br>  C | 256 |
| N20RI:      | TCCTCGAGIACGTAICCGTA<br>  T    A  A    A     A<br>         T<br>         C | 64 |

*A: adenine, T: thymine, G: guanine, C: cytosine, I: inosine

4. Preparation of Poly(A)$^+$ RNA

From tubers of potato variety Brodick stored at 5° C. for 4 months, or from sprouts of potato variety Record or Brodick, the total RNAs were isolated by the SDS-phenol method. Poly(A)$^+$ RNAs were purified from the total RNAs using a Dynabeads mRNA purification kit (DYNAL) according to the manual attached to the kit.

5. Synthesis of cDNA Using the thus isolated poly(A)$^+$ RNAs as templates and oligo dT(12–18) or random hexanucleotide as a primer, and using RNase H-free reverse transcriptase (BRL), single-stranded cDNAs were firstly prepared. Then double-stranded cDNAs were prepared using a cDNA synthesis kit (Amersham). The single-stranded cDNAs synthesized here were used as the templates in the PCR described below, and the double-stranded cDNAs thus prepared were used for the preparation of the cDNA library described below. The method for synthesizing the cDNAs was in accordance with the manual attached to the reagent or the kit.

6. Preparation of λgt10 cDNA Library

Using the double-stranded cDNAs prepared from the poly(A)+ RNAs from tubers of variety Brodick, which were synthesized using oligo dT (12–18) as a primer, or using the double-stranded cDNAs prepared from the poly(A)+ RNAs from the sprouts of tubers of variety Record, which were synthesized using the random hexanucleotide, λgt10 cDNA libraries were prepared. The libraries were prepared by using a λgt10 cloning kit (Amersham) according to the manual attached to the kit. However, the adaptor included in the kit was not used and an Eco RI/Not I adaptor (Pharmacia LKB) was used therefor.

7. Isolation of cDNA Encoding N-terminal Region of Purified PFK

PCR was performed using 500 pmol each of N10 and N20RI (see Table 2) synthesized by a DNA synthesizer based on the amino acid sequence shown in Table 1 as primers, and using 1.0 μg of the single-stranded cDNA originated from the genomic DNA of variety Record or 0.1 μg of the single-stranded cDNA originated from the poly (A)+ RNAs from tuber sprouts of variety Brodick as a template. The buffer which was supplied with the Taq polymerase (Ampli Taq, Perkin-Elmer Cetus) was used according to the manual attached thereto. To the reaction mixture, 2.5 U of the enzyme and 20 nmol each of the nucleotides were added to the reaction mixture and the total volume of the reaction mixture was 100 μl. A cycle of 94° C., 1 minute (denaturing)/50° C., 2 minutes (annealing)/72° C., 2 minutes (extension) was repeated 35 times and then the reaction was further continued at 72° C. for 10 minutes. An aliquot of the reaction mixture was sampled and analyzed by 4% agarose gel electrophoresis. A PCR product having 59 base pairs was detected in both cases where either of the DNAs was used as the template. These DNAs of 59 base pairs were subcloned into plasmid vector pCR1000 (Invitrogen) according to the manual attached to the kit. As a result, a number of E. coli colonies having recombinant plasmids were obtained. Plasmids were recovered by a conventional method from 7 clones (i.e., 4 clones originated from Record genomic DNA and 3 clones originated from Brodick cDNA) having the plasmid containing the insert of 59 base pairs. The DNA sequences of the PCR products contained in the 7 clones were determined by the dideoxy chain termination method. The DNA sequences were determined using SEQUENASE Var2 (U.S. Biochemical Corp) according to the manual attached thereto. Among the 7 clones, 6 clones had the same DNA sequence (23 base pairs) in the region between the PCR primers. A DNA having the 23 base pairs was synthesized by a DNA synthesizer, and was named PFK23 (Table 3). PFK23 was used as a primer in the PCR described below and as a probe for screening the cDNA library.

TABLE 3

DNA Sequence of PFK23 (5' → 3')

ATGAAGGTGGTGAAAGGAGATTA

8. Isolation of PFK cDNA with Partial Length

The μgt10 cDNA library (150,000 pfu) originated from tuber sprouts of variety Record was amplified by the plate lysate method and the λDNA was purified. PCR was performed using 1.0 μg of the obtained EDNA as a template, and using 100 pmol each of PFK23 and μ1232 (Table 4) which has the DNA sequence of λgt10. The reaction conditions of the PCR were the same as described above except that the temperature in annealing was 60° C. As a result, a PCR product having about 600 base pairs was obtained. The obtained PCR product was subcloned in the above-mentioned plasmid vector pCR1000, and one of the obtained recombinant plasmids was named pPFK01. The DNA sequence of the PCR product inserted in plasmid pPFK01 was determined by the method described above. The amino acid sequence was deduced from the DNA sequence. As a result, a part of the amino acid sequence had a significant homology with the amino acid sequence of known PFKs. Further, in the 5'-terminal region, the DNA sequence encoded the amino acid sequence determined by the analysis of the purified PFK mentioned above.

9. Isolation of PFK cDNA with Full Length

The DNA fragment having about 600 base pairs obtained by digesting the plasmid pPFK01 with restriction enzyme Not I was labelled with a radioactive isotope $^{32}$p. Using the labelled DNA as a probe, the λgt10 cDNA library (about 400,000 pfu) originated from tubers of variety Brodick was screened by the plaque hybridization method. As a result, 57 independent positive plaques were obtained. From these plaques, 24 plaques were randomly selected and were subjected to secondary screening using the above-mentioned DNA fragment having about 600 base pairs and PFK23 as the probes. As a result, 11 clones were positive to both labelled probes. After third screening, plate lysates were prepared from these independent 11 clones. PCR was performed using 10 μl of the lysate as a template and 50 pmol each of the synthetic DNAs λ1232 and λ1231 shown in Table 4 as primers. The PCR was performed in the same conditions as described above except that the annealing temperature was 60° C. By analysis of the PCR product by 0.8% agarose gel electrophoresis, it was estimated that the length of the cDNA fragment per se excluding the length of the λDNA was about 1700–2200 base pairs. Potato tuber poly(A)+ RNA was analyzed by the conventional Northern blotting method using as a probe the above-mentioned DNA fragment of about 600 base pairs labelled with radioactive isotope $^{32}$p. As a result, a poly(A)+ RNA having about 2000–2300 base pairs was detected, which is almost coincident with the results of the above-described PCR. The recombinant plasmid vectors prepared by subcloning the DNA insert cut out by restriction enzyme Not I from the 11 λgt10 clones into the Not I site of a plasmid vector pBluescript SK II(-) (Stratagene) were named pPFK16, pPFK17, pPFK19, pPFK26, pPFK28, pPFK29, pPFK31, pPFK32, pPFK33, pPFK34 and pPFK35, respectively.

TABLE 4

DNA Sequence of Primers Originated from λgt10 used in PCR (5' → 3')

| λ1232: | CTTATGAGTATTTCTTCCAGGGTA |
|---|---|
| λ1231: | AGCAAGTTCAGCCTCGTTAAG |

The total DNA sequence (1978 base pairs) of the cDNA insert in pPFK32 was determined by the method described above, and is shown as Sequence ID No. 1 in the Sequence Listing together with the deduced amino acid sequence encoded thereby. The DNA contained a region of 1455 base pairs translated into 485 amino acids containing the determined amino acid sequence of the N-terminal of the purified PFK (i.e., the third amino acid, threonine to the 26th amino acid, leucine (although the 24th and 25th amino acid of the purified PFK could not be determined, as shown in Table 1)

shown in Sequence ID No. 1 in the Sequence Listing). In the deduced amino acid sequence, an initiation codon encoding methionine exists upstream of the N-terminal of the purified potato tuber PFK polypeptide by two amino acids. The deduced molecular weight is 53.8 kDa which is almost coincident with the molecular weight (53 kDa) of the potato tuber PFK-d polypeptide, which was deduced by Kruger et al (Arch. Bioichem. Biophys. 267, 690–700, 1988). The reason why the codon "ATG" of 133rd to 135th nucleotides is the initiation codon of PFK is that termination codons in different reading frames exist upstream of this ATG (e.g., TGA: 15th–17th, TAA: 26th–28th, and TGA: 55th–57th), so that even if an ATG codon exists upstream of the first base C of the isolated cDNA, the codon cannot be the initiation codon of PFK. Further, although an ATG codon exists at 36th–38th nucleotides, a termination codon TGA exists at 90th - 92nd nucleotides in the same reading frame, so that the ATG codon cannot be the initiation codon of PFK.
<Characterization of PFK Encoded by Isolated cDNA>
10. Expression of Plant PFK Gene in *E. coli*

To prove that the isolated gene is the gene encoding PFK having an enzyme activity, it is necessary to actually express the gene. Therefore, the inventors tried to express the isolated gene by introducing it into *E. coli* as follows.

First, PCR was performed using 250 ng of plasmid pPFK32 as a template and 30 pg each of PFK32 and PFK32R (Table 5) to which Eco RI site and Pst I site had been introduced, respectively, as primers. The reaction conditions were the same as described above except that the annealing temperature was 30° C., 35° C. or 40° C., the number of cycles was five, and Pfu DNA polymerase (Stratagene) was used as the DNA polymerase. The obtained PCR product was fractionated by 0.8% agarose gel electrophoresis and the desired band corresponding to about 1800 base pairs was cut out. The DNA in the cut out band was recovered from the gel by a conventional method. The DNA thus obtained, having about 1800 base pairs, was digested with restriction enzymes Eco RI and Pst I, and the resultant was ligated with plasmid vector pKK223–2 (Pharmacia LKB) which had been digested with restriction enzymes Eco RI and Pst I. The resulting recombinant plasmid (pKK32) was introduced into *E coli* XL1-Blue (Biotechniques, 5, 376–378, 1987) according to a conventional method and the *E. coli* was cultured overnight at 37° C. on Luria-Bertani (hereinafter referred to as "LB") agar medium containing antibiotic carbenicillin (50 μg/ml). From a number of emerged colonies, 110 colonies were selected. The DNA fragment having about 2000 base pairs, which was cut out from the plasmid pPFK32 by restriction enzyme Not I, was labelled with a radioactive isotope $^{32}$p and colony hybridization was performed using the labelled DNA as a probe. As a result, 66 positive colonies were obtained. These *E. coli* clones, which were confirmed to contain the potato PFK gene, could hardly grow on the LB agar medium containing 1 mM of isopropylβ-D-thiogalactopyranoside (hereinafter referred to as "IPTG") presumably because the metabolism is confused by the PFK of which activity is controlled in a different manner from that of the *E. coli* PFK. Thus, the PFK gene introduced into *E. coli* was expressed as follows. Firstly, the *E. coli* cells were cultured with shaking at 37° C. on LB liquid medium containing 50 μg/ml of carbenicillin until the absorbance at 600 nm reached 0.3–0.7. Then IPTG (1 mM) was added and the cells were recovered after culturing the cells with shaking for a prescribed time. The cells were then lyzed by the method of Tabita et al (Anal. Biochem. 84, 462–472, 1978) using toluene, and the PFK activity was measured by the method of Kruger et al (Arch. Bioichem. Biophys. 267, 690–700, 1988). *E. coli* No. 58 showed a PFK activity which is about 7 times higher than that of the control *E. coli* No. 1 (into which pKK223–2 was introduced) (FIG. 1).

TABLE 5

DNA Sequences of PCR Primers Containing
Introduced Eco RI site and Pst I site (5' → 3')

\* \* \* \*
PFK32:   TATATATTTGGAATTCATGGGTACTGAG
         Eco RI

\* \*
PFK32R:  CAAAAGACCCTGCAGCCACACAG
         Pst I

\*: mismatched region

To determine whether the high PFK activity of *E. coli* No. 58 was due to the plant PFK activity or to the PFK activity of *E. coli* XL1-Blue, immunotitration was performed according to the method of Kruger et al (Arch. Bioichem. Biophys. 267, 690–700, 1988).

Figure 2:
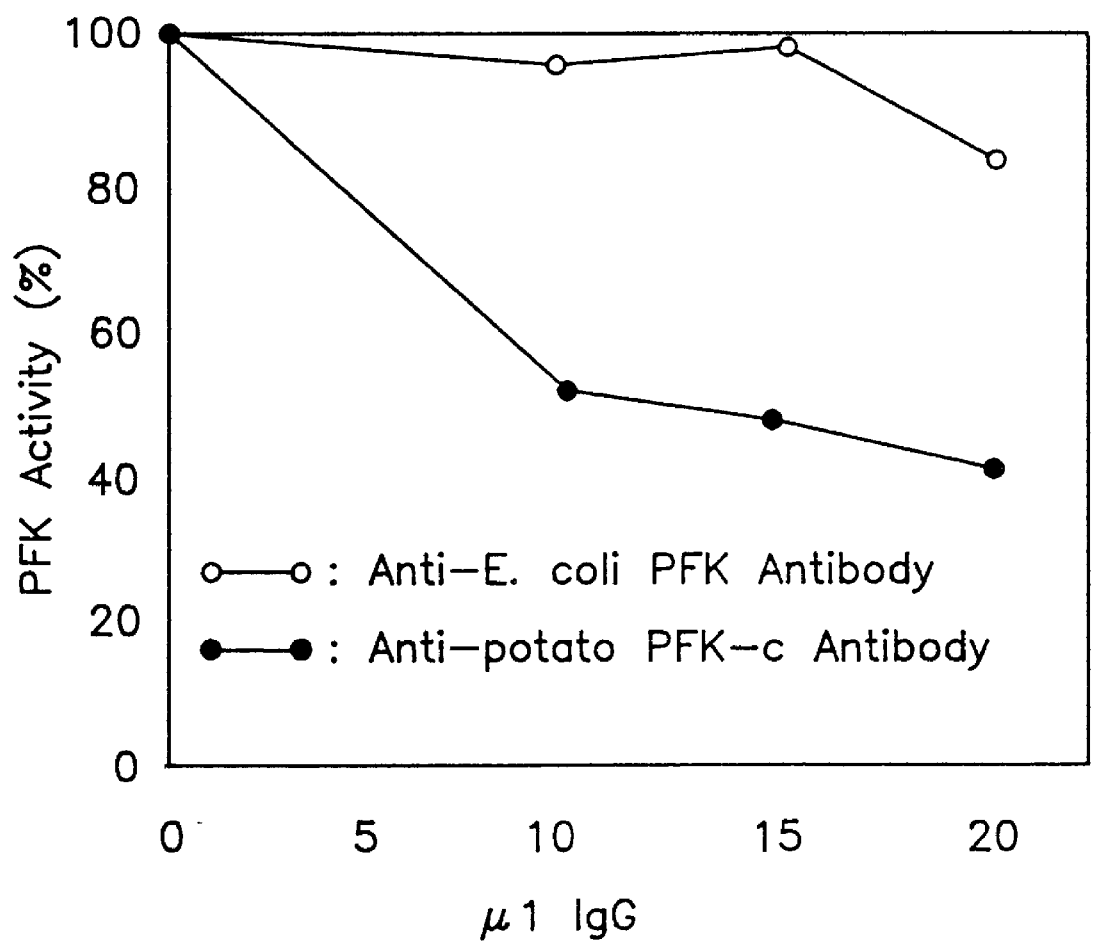
FIG. 2 shows the results of immunotitration of the PFK activity of E. coli No. 58 transformed with the recombinant vector according to the present invention.

In the immunotitration, the high PFK activity of *E. coli* No. 58 was not substantially reduced by anti-*E. coli* PFK antibody, but was significantly reduced by anti-potato PFK-c antibody (presented by Dr. Kruger, the Department of Plant Sciences, University of Oxford) (FIG. 2). It has been confirmed by Western blot analysis and by immunotitration that the anti-potato PFK-c antibody strongly reacts with potato PFK-c and PFK-d, but does not substantially react with *E. coli* PFK.

These results established that the protein expressed in *E. coli* No. 58 after induction by IPTG was potato PFK, and that the cDNA inserted in the plasmid pPFK32 was a potato PFK gene.

11. Comparison of Amino Acid Sequence between Potato PFK and PFKs of Other Organisms The amino acid sequence deduced from the DNA sequence of the cDNA contained in pPFK32, which encodes potato PFK, was compared with amino acid sequences of known PFKs using a database (The Swiss Prot data bank (Release 23)). Although the amino acid sequence has not more than 30 percent identity with the reported PFKs, the homologous regions are concentrated in the binding sites of the substrate, coenzyme and of the regulatory substance which characterize PFK (Evans, P. R and Hudson, P. J. (1979) Nature, 279, 500–504) and in the vicinity thereof. The region showing significant homology is approximately 98th–321st amino acids, and little significant homology with the reported PFKs of other organisms is found in the N-terminal and C-terminal regions of 1st–97th amino acids and 322–485 amino acids, respectively. The reported eukaryotic PFKs have a duplicate structure in which a single polypeptide chain contains both a catalytic site to which F6P binds and a regulatory site to which fructose-2,6-bisphosphate binds, the regulatory site has a similar amino acid sequence to the catalytic site. It was shown that the amino acid sequence deduced from the DNA sequence of the plant PFK gene isolated by the present invention does not have such a structure. Further, there are as many as several tens of amino acids, including some with putative F6P binding sites, which are commonly conserved in the PFKs of other organisms but are not conserved in the potato PFK. These facts suggest that the plant PFK has a structure and function different from those of the reported PFKs.

It is said that there are two kinds of PFKs in plants, that is, plastidic PFK and cytoplasmic type PFK. The PFK encoded by the potato PFK cDNA according to the present invention has a N-terminal longer than the purified protein by two amino acids (Met, Gly). It is not clear whether this difference was caused by degradation during the purification or by processing performed in the cells. However, it was shown that the PFK does not have a transit peptide taking part in the transport of a polypeptide to plastids such as the amyloplast and chloroplast, so that the PFK is cytoplasmic.

12. Purification of Potato PFK Expressed in *E. coli*

Figure 3A:
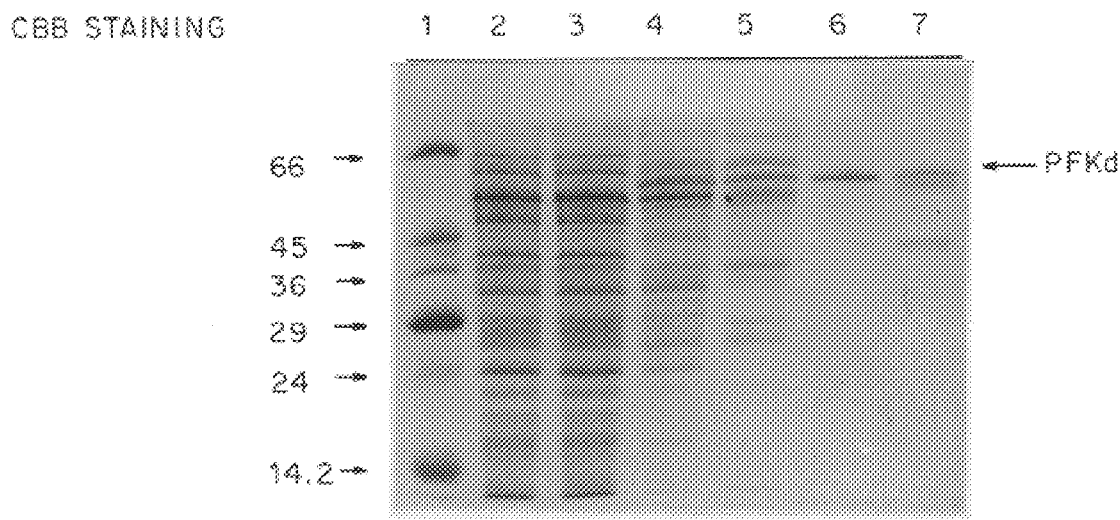
FIGS. 3A–3B show the results of the analyses by SDS-PAGE and Western blot of the PFK purified from E. coli No. 58 transformed with the recombinant vector according to the present invention.
Figure 3B:
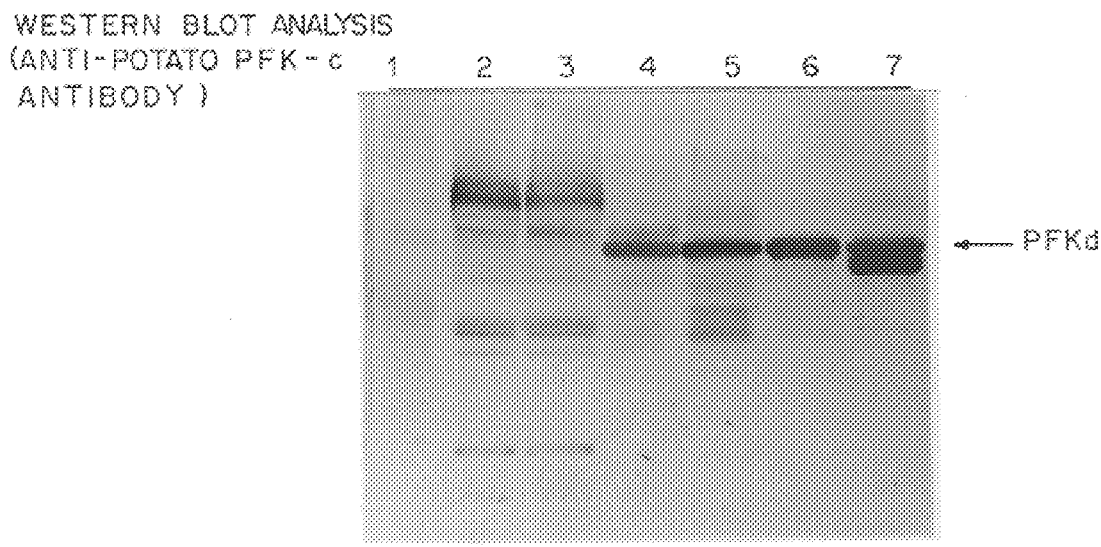

Potato PFK was purified from *E. coli* No. 58, which was confirmed to express potato PFK by the following method, and its stability under low temperatures was examined. About 0.3 g of cells were suspended in an extraction buffer (100 mM Tris-HCl (pH 8.0), 2 mM $MgCl_2$, 1 mM EDTA, 14 mM 2-mercaptoethanol, 1 mM PMSF, 1 $\mu$M leupeptin and 1 NM pepstatin) and disrupted by ultrasonication. The resultant was centrifuged at 50,000×g for 30 minutes and the supernatant was recovered. The supernatant was then applied to a Cibacron Blue agarose (type 3000-CL, Sigma) column (16×55 mm) which had been equilibrated with buffer A prepared by adding glycerol to the extraction buffer to 10% (v/v). By this operation, most of the *E. coli* PFK was strongly bound to the gel and most of the potato PFK was not bound to the gel, so that the latter was recovered in the flow through fraction. The thus recovered solution was then applied to a Reactive Red 120-agarose (type 3000-Cl, Sigma) column (16×110 mm) equilibrated with buffer A to adsorb the PFK on the gel. After washing the column with 25 ml of buffer A, PFK was eluted by 150 ml of buffer A having a linear gradient of 0–1.0M KCl. The fractions containing PFK activity were combined and concentrated to 3 ml by ultrafiltration (Amicon PM10 membrane). The resultant was desalted by a Biogel P-6 column (Bio-Rad) equilibrated with buffer A. Finally, the desalted sample was applied to a Mono Q column (0.5×50 mm, Pharmacia LKB) equilibrated with buffer A. After washing the column with 5 ml of buffer A, PFK was eluted by 150 ml of buffer A having a linear gradient of 0–1.0M KCl. The fractions having PFK activity were combined to obtain a purified sample. After fractionating the purified sample by urea/SDS-PAGE, the gel was stained by CBB. On the other hand, after fractionating the purified sample by urea/SDS-PAGE, the polypeptide was transferred to a nitrocellulose filter and was subjected to Western blot analysis using the anti-potato PFK-c antibody. In both analyses, a polypeptide with a molecular weight of 53 kDa was detected (FIG. 3). Thus, it was proved that the isolated PFK encodes PFK-d.

13. Confirmation of Stability at Low Temperature of Potato PFK Expressed in *E. coli*

Using the purified PFK thus obtained, the low temperature stability of the enzyme activity was examined in the temperature range of 0°–25° C. by the method of Hammond et al (Planta 180, 613–616, 1988). As an indicator expressing the stability of the enzyme at low temperatures, Q10 value was used. Taking the temperature along the X axis and taking the logarithm of the enzyme activity along the Y axis, an equation of $$dy/dx = 0.1 \log Q10$$

is satisfied, wherein dy/dx means the slope in the above-mentioned coordinates. The PFK expressed in *E. coli*, which originated from potato variety Brodick, had a Q10 value at 0° C. of as low as 2.42, which is not much larger than the Q10 value at room temperature, that is 1.66 (Table 6). The PFK encoded by the cDNA inserted in the plasmid pPFK32 had a Q10 value at 5° C. of 2.24. The Q10 value at 5° C. of *E. coli* PFK-1 is 2.89 (Kruger, N. J. (1989) Biochemical Society Transaction 629th Meeting, London Vol. 17, 760–761), and the Q10 values at 2°–6° C. of the PFKs in the tubers of potato variety Record, which undergoes Cold Induced Sweetening, are 3.10 (PFK III) and 4.20 (PFK IV), respectively (Hammond, J. B. W. et al. Planta (1990) 180, 613–616). Thus, it was proved that the PFK encoded by the potato PFK gene isolated in the present invention has a significantly higher cold stability than the *E. coli* PFK and the PFKs of the potato variety which undergoes Cold Induced Sweetening. On the other hand, ap Rees et al reported that the Q10 value at 2°–10° C. of SPS, which is the rate-determining enzyme in the sucrose synthesis pathway and which competes with PFK for the substrate F6P, is 2.25 (Plants and Temperature (ed. Long, S. P. and Woodward, F. I.) Society of Experimental Biology Seminor Series No. 42, Cambridge, U.K.; Cambridge University Press, pp.377–393). Thus, the PFK encoded by the DNA according to the present invention has cold stability comparable to that of SPS (Table 6). Therefore, by expressing the PFK gene according to the present invention under the control of a promoter which is strongly expressed in the tubers stored at a low temperature, a potato variety having low sucrose content in the tubers stored at low temperature can be developed, so that a potato variety resistant to Cold Induced Sweetening (i.e., the content of glucose and fructose is low) can be prepared.

TABLE 6

| | Q10 Values of Potato PFK Expressed in *E. coli* | | | | | | | |
|---|---|---|---|---|---|---|---|---|
| Temperature (°C.) | 0 | 1 | 2 | 5 | 7 | 10 | 15 | 20 | 25 |
| Q10 Value | 2.42 | 2.38 | 2.35 | 2.24 | 2.18 | 2.10 | 1.93 | 1.79 | 1.66 |

14: Isolation of PFK Genes from Various Plants

Isolation of PFK genes from various plants was tried using the isolated potato PFK cDNA. Messenger RNAs were isolated from a callus originated from rice (variety: Tsukinohikari) immature embryo, a callus originated from maize endosperm and from green leaves of Flaveria and green leaves of radish by the method described for potato, and cDNA libraries were prepared by the following method. That is, the cDNA libraries of rice, Flaveria and radish were prepared using TimeSaver cDNA Synthesis Kit (commercially available from Pharmacia), λ ZAP II Cloning Kit (commercially available from Stratagene) and Gigapack II Gold (commercially available from Stratagene) in accordance with the manuals attached to the commercial products. The cDNA library of maize was prepared using cDNA Synthesis Kit (commercially available from Amersham) and λ gt10 cDNA Cloning Kit (commercially available from Amersham) in accordance with the manuals attached to the commercial products.

From the prepared cDNA libraries, λ phages in which PFK cDNAs were incorporated were isolated by the plaque hybridization method. In this operation, the DNA fragment of about 2 kbp obtained by digesting the above-mentioned plasmid pPFK32 with Not I was used as a probe after labelling the fragment with radioactive $^{32}p$. From all of the cDNA libraries, positive plaques which react with this probe were obtained. As for the maize PFK cDNA, λ DNA purified by the plate lysate method was digested with Eco RI and the insert containing the PFK cDNA was subcloned into a plasmid pBluescript SK II(−) (commercially available from Stratagene). Thereafter, the DNA sequence was determined by the method described for potato PFK. As for cDNAs of other plants, the inserts were subcloned into a plasmid pBluescript SK(−) (commercially available from Stratagene) using the helper phage (ExAssist helper phage (M13)) and E. coli (SOLR strain) contained in the λ ZAP II Cloning Kit (commercially available from Stratagene) in accordance with the manual attached to the kit. Thereafter, the DNA sequence was determined by the method described for potato PFK. The nucleotide sequences of the cDNAs of Flaveria, rice, maize and radish PFKs are shown in Sequence ID Nos. 3, 5, 7 and 9, respectively, and the deduced amino acid sequences encoded by the cDNAs are shown in Sequence ID Nos. 4, 6, 8 and 10, respectively. All of the amino acid sequences of the plant PFKs showed very high homology with the amino acid sequence of the potato PFK-d (Sequence ID No. 2), while their homologies with the reported PFKs of other organisms such as bacteria, mammals and yeasts were significantly lower. The plants from which PFK genes were isolated include a wide variety of plants. That is, they include both monocotyledons (rice and maize) and dicotyledons (Flaveria, potato and radish), and include the families Gramineae (rice, maize), Compositae (Flaveria), Solanaceae (potato) and Cruciferae (radish). Thus, it was proved that the potato PFK cDNA shown in Sequence ID No. 1 can be used for isolating PFK genes of a wide variety of plants.

By comparing the amino acid sequences of the PFKs of the various plants, 13 amino acid sequences (having not less than 5 amino acid residues) which are common to all of these plants were discovered (Table 7). These amino acid sequences include those specific to plants (Sequence ID Nos. 11, 14, 21 and 22) which do not exist in the reported PFKs of other organisms. Particularly, the amino acid sequence shown in Sequence ID No. 22 is thought to correspond to the amino acid sequence (in the vicinity of Leu Gly His Val Gln Arg Gly Gly) defining the binding site of the substrate F6P and vicinity thereof (Evans, P. R. and Hudson, P. J. (1979) Nature, 279, 500–504). The amino acid sequence of the binding site and the vicinity thereof is very well conserved in other organisms (Heinisch, J. et al., (1989) Gene, 78, 309–321). However, plants do not have this amino acid sequence but have the amino acid sequence shown in Sequence ID No. 22 as a consensus sequence.

Thus, it was proved that the cDNA of potato PFK having the nucleotide sequence shown in Sequence ID No. 1 is useful as a probe for isolating the PFK genes of other plants. Further, by comparison of the amino acid sequences of PFKs of various plants, amino acid sequences which are thought to commonly exist in plants were identified (Table 7). These amino acid sequences are useful, for example, for synthesizing primers for isolating a PFK gene from a plant by the PCR method. Still further, amino acid sequences which are thought to commonly exist in PFKs of plants but not exist in PFKs of other organisms were identified. That is, by the present invention, the amino acid sequences characteristic to plants (i.e., amino acid sequences shown in Sequence ID Nos. 11, 14, 21 and 22) were first identified.

TABLE 7

Consensus Amino Acid Sequences in PFKs of Various Plants
(Numbering corresponds to the amino acid residue number in Sequence ID No. 1) (SEQ ID NO:10)

| | | | | | | | | | | | | |
|---|---|---|---|---|---|---|---|---|---|---|---|---|
| (1) | Arg | Ala | Gly 80 | Pro | Arg | | | | | | | (SEQ ID NO:11) |
| (2) | Ile | Val | Thr | Cys | Gly 100 | Gly | Leu | Cys | Pro | Gly 105 | Leu | Asn | (SEQ ID NO:12) |
| (3) | Gly | Tyr | Arg | Gly 135 | Phe | | | | | | | (SEQ ID NO:13) |
| (4) | Ile | Val | Asp | Ser 175 | Ile | Gln | | | | | | (SEQ ID NO:14) |
| (5) | Pro | Lys | Thr | Ile | Asp 220 | Asn | Asp | Ile | | | | (SEQ ID NO:15) |
| (6) | Phe 230 | Gly | Phe | Asp | Thr | Ala 235 | Val | Glu | | | | (SEQ ID NO:16) |
| (7) | Ala | Gln 240 | Arg | Ala | Ile | Asn | | | | | | (SEQ ID NO:17) |
| (8) | Val 260 | Lys | Leu | Met | Gly | Arg 265 | | | | | | (SEQ ID NO:18) |
| (9) | Ser | Gly | Phe | Ile 270 | Ala | | | | | | | (SEQ ID NO:19) |
| (10) | Ala | Glu | Gly 320 | Ala | Gly | Gln | | | | | | (SEQ ID NO:20) |
| (11) | Asp | Ala | Ser 340 | Gly | Asn | | | | | | | (SEQ ID NO:21) |
| (12) | Leu 370 | Lys | Tyr | Ile | Asp | Pro 375 | Thr | Tyr | Met | | | (SEQ ID NO:22) |
| (13) | Cys | Leu 285 | Ile | Pro | Glu | | | | | | | (SEQ ID NO:23) |

15: Construction of Plasmid Vector for Transforming Plants

Figure 4:
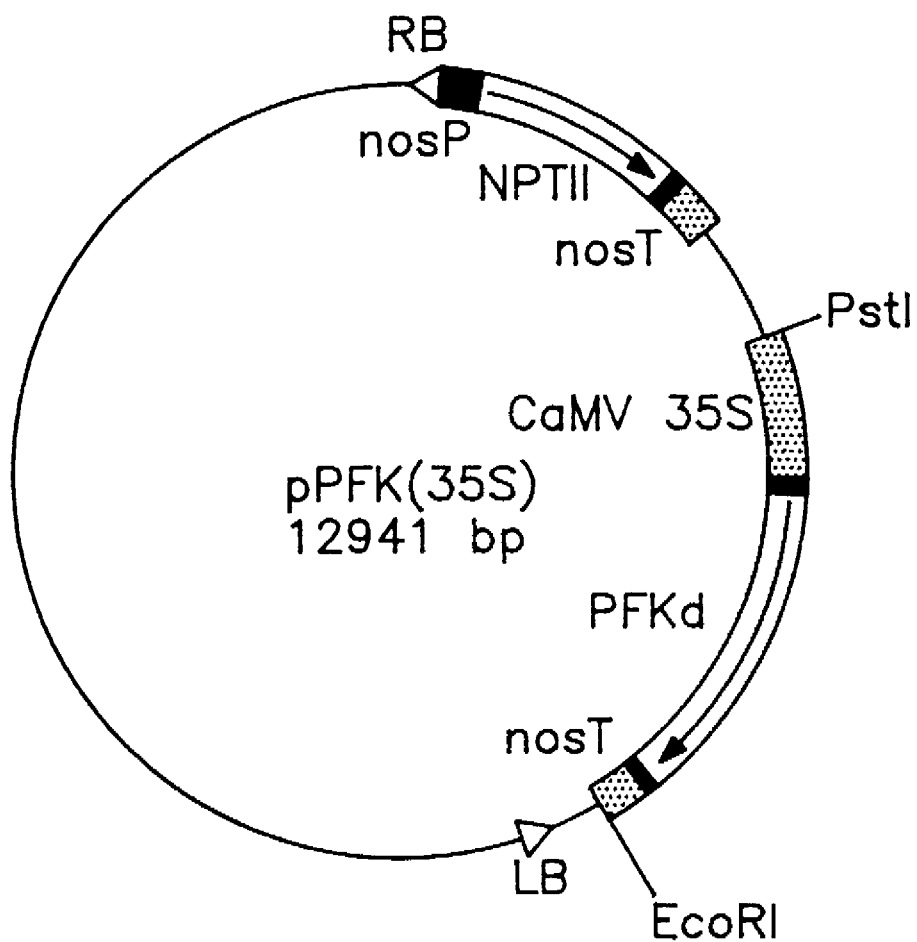
FIG. 4 shows an expression vector containing cold stable PFK-d gene.

To introduce the cold stable PFK gene of potato variety Brodick into a plant, a plasmid pPFK(35S) shown in FIG. 4 was prepared. The method for preparing the plasmid pPFK (35S) will now be described in detail. Firstly, a polylinker containing recognition sites of Hind III, Not I, Bgl II, Bam HI, Eco RI, Sma I, Pst I, Sst I, Bcl I, Bgl II, Not I and Eco RI in the order mentioned (commercially available from Agricultural Genetics Company, Cambridge, United Kingdom) was ligated to pUC19 preliminarily digested with Hind III and Eco RI. The obtained plasmid was named pUC19(PL). The polyadenylation signal sequence (about 0.3 kbp) of nopaline synthetase gene, which was obtained by digesting a plasmid pAPT9 (commercially available from Agricultural Genetics Company, Cambridge, United Kingdom), was ligated to pUC19(PL) preliminarily digested with Sst I and Bcl I. The obtained plasmid was named pUC19 (nos term). Then a DNA fragment of about 2.3 kbp containing a patatin promoter sequence was excised from a plasmid pBI240.7 (Bevan et al., Nucleic Acid Research 14: 4625–4638, 1986) with Bgl II and Bam HI, and this DNA fragment was ligated to pUC19 (nos term) preliminarily digested with Bgl II and Bam HI. The obtained plasmid was named pUC19(pat/nos term). Thereafter, the cold stable PFK gene (about 1.8 kbp) was excised from the above-described plasmid pKK32 with Eco RI and Pst I and ligated to pUC19(pat/nos term) preliminarily digested with Eco RI and Pst I. The obtained plasmid was named pPFK(pat). The plasmid pPFK(pat) was digested with Eco RI and the resultant was blunted with Klenow fragment of $E.\ coli$ DNA polymerase I. Finally, the thus obtained plasmid was digested with Sst I and the excised cold stable PFK gene of about 1.8 kbp was ligated to a plasmid pROK2 (originating from pBin19: Baulcombe, D. et al., (1986), Nature, 321, 446–449) preliminarily digested with Sma I and Sst I. The thus obtained plasmid was named pPFK(35S) (FIG. 4) wherein the terms used therein have the following meanings:

RB,LB:right and left borders of T-DNA of *Agrobacterium tumefaciens*.

nosP:promoter (0.3 kb) of the nopaline synthase gene of *A. tumefaciens*.

NTPII:neomycin phosphotransferase gene (1.2 kb), conferring kanamycin resistance.

nosT:polyadenylation signal (0.3 kb) of the nopaline synthase of *A. tumefaciens*.

CaMV 35S:35S promoter (0.8 kb) from cauliflower mosaic virus.

PFKd:cold tolerant PFK gene (1.8 kb) from potato cv. Brodick.

16: Transformation of Potato

The vector plasmid pPFK(35S) shown in FIG. 4 was introduced into *Agrobacterium tumefaciens* LBA4404 by the electroporation method (Shen, W.-J. and Forde, B. G. (1989) Nucleic Acid Research 17, 8385), and the obtained strain was named LBA4404(35S/PFKd). The strain LBA4404(35S/PFKd) was used to transform potato variety Bintje as an example of plants. The method for the transformation will now be described in detail. Virus-free sterilized plants of potato variety Bintje were purchased from Scottish Agricultural Services Agency, Edinburgh, United Kingdom. From the purchased in vitro plants, a plurality of single nodes were aseptically cut out and each single node was cultured on a solid medium containing inorganic salts of Lismaier and Skoog's medium (hereinafter referred to as "LS medium") (Lismaier, E. and Skoog, F. (1965) Physiol. Plant, 18, 100–127), 30 g/l of sucrose and 8 g/l of agar. The stems and leaves of the plants were used for the transformation described below. That is, sections (having a length of 0.5–2.0 cm) of the stems or sections (having a length of about 0.6–1.0 cm in the longitudinal direction and about 0.5–1.0 cm in the transverse direction) of the leaves were cultured together with LBA4404(35S/PFKd) in a liquid medium containing the inorganic salts of LS medium and 30 g/l of glucose at 25° C. for 48 hours. The population density of LBA4404(35S/PFKd) at the beginning of this culture was adjusted to about $10^8$ cells/ml. After this culture, sections of the stems or leaves were washed with sterilized water containing 250 mg/l of cefotaxime several times and placed on KS1 medium reported by Kasaoka et al (Japanese Laid-open Patent Application No. 6–133783). Calli resistant to kanamycin emerged about 20 days after the beginning of this culture. By continuing the culture for another 10–30 days, plants were regenerated from the calli. The kanamycin-resistant plants were cut into single nodes and each of the single nodes was cultured on a solid medium containing inorganic salts of LS medium, 30 g/l of sucrose, 250 mg/l of cefotaxime, 100 mg/l of kanamycin and 8g/l of agar to grow kanamycin-resistant plants. The plants were transplanted to pots' and cultivated in a green house. As a control, non-transformed potato variety Bintje was used. The control plants were aseptically grown in test tubes in the same manner as the transformed plants and then cultivated in pots in a green house. When the transformed plants and control plants completely wilted naturally after about 4 months from the transplantation to the pots, potato tubers were harvested. The harvested tubers were stored in a cold storeroom (5°–8.5° C. or 15° C.). These tubers were used for the various analyses described below.

17: Generation of Cold Stable PFK in Transformed Potato

DNAs were extracted from the non-transformed line B40 and transformed line B75 having resistance to kanamycin by CTAB method (Doyle, J. J. and Doyle, J. L. (1987) Phytochemical Bulletin, 19, 11–15), and were subjected to Southern analysis in accordance with the method of Sambrook et al (Molecular Cloning: A Laboratory Manual/Second Edition, Cold Spring Harbor Laboratory Press, 1989). More particularly, the DNAs were digested with Eco RI and the resulting DNA fragments were blotted on a nylon membrane. The blots were then reacted with a probe labelled with radioactive $^{32}p$. As the probe, nos terminator region (280 bp) or the 3' flanking region (235 bp) of the cold stable PFK gene, which is excised from the above-mentioned plasmid pKK32 with Bgl I and Pst I, was used. It was confirmed that in line B75, 5 copies of the gene per tetraploid genome were introduced when any of the DNA fragments was used as the probe (data not shown).

Figure 5:
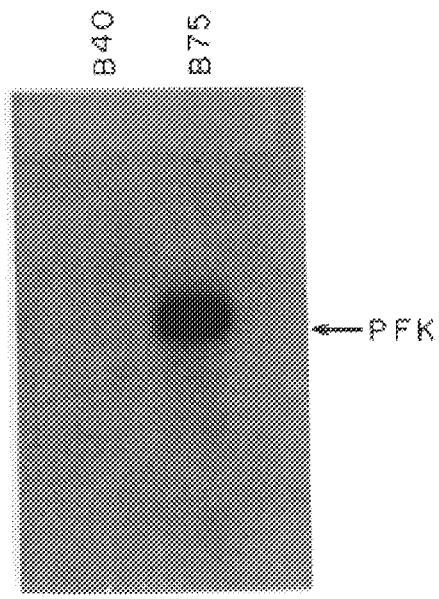
FIG. 5 shows the results of Northern analyses of RNAs from stored tubers of lines B75 and B40.

RNAs were purified from the tubers (stored at 15° C. for 2 months) of line 40 or line B75 cultivated in pots in a green house, and the purified RNAs were subjected to Northern analysis according to the method of Sambrook et al (Molecular Cloning: A Laboratory Manual/Second Edition, Cold Spring Harbor Laboratory Press, 1989). As the sample, 25 μg of the total RNAs was used. As the probe, the 3' flanking region (235 bp) of the cold stable PFK DNA, excised by digesting the above-described plasmid pKK32 with Bgl I and Pst I, was used after labelling the DNA with radioactive 32p. The results are shown in FIG. 5. Very strong signals were observed for the line B75 but no PFK mRNA was detected for the non-transformed line B40. From the experiences of the present inventors, it is difficult to detect the PFK mRNA in potato tubers by Northern analysis unless a purified mRNA, not the total RNAs, is used. Presumably an extremely large amount of PFK mRNA is expressed in tubers of line B75, which never occurs in normal potatoes, and such excess production of PFK mRNA is thought to be the transcript of the introduced cold stable PFK gene.

Figure 6:
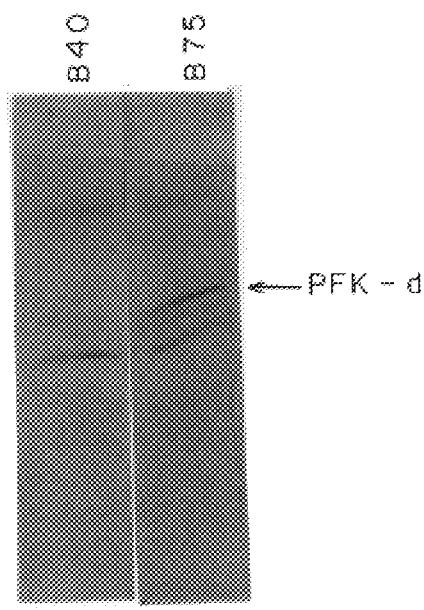
FIG. 6 shows the results of Western analyses of proteins from stored tubers of lines B75 and B40.

From the tubers of line B75 or line B40, which were stored at 15° C. for 2 months after harvest, crude extracts were prepared according to the method of Kruger et al (Kruger, N. J. et al., (1989) Arch. Biochem. Biophys. 267, 690–700) and subjected to Western analysis. As the antibody, the above-mentioned anti-potato PFK-c antibody was used. The results are shown in FIG. 6. Among the polypeptides which reacted specifically or non-specifically with the antibody employed, the polypeptide which was different in amount was PFK-d alone. The intensity of the bands in the Western analysis suggest that, in tubers of line B75, polypeptide PFK-d is present at 3–4 times the level in the control line B40. This is in general agreement with the results of the Northern analysis described above. However, the amount of polypeptide PFK-d in line B75 was smaller than expected from PFK poly(A)$^+$ RNA detected. This is presumably because the amount of protein expressed from poly(A)$^+$ RNA derived from the foreign PFK gene is not commensurate with the protein expressed from poly(A)$^+$ RNA derived from the endogenous PFK genes.

From tubers (stored at 15° C. for two months after harvest) of lines B75 and B40, crude extracts were prepared according to the method of Kruger et al (Kruger, N. J. et al., (1989) Arch. Biochem. Biophys. 267, 690–700) and PFK activities were determined. One tuber was used for each measurement, and the average of three measurements is shown in Table 8. As shown in Table 8, it was confirmed that line B75 had a total PFK activity 1.3 times higher than that of line B40. The total PFK activities means the total of the activities of PFK I, II, III and IV constituted by various combinations of four polypeptides PFK-a, PFK-b, PFK-c and PFK-d reported by Kruger et al (Kruger, N. J. et al., (1989) Arch. Biochem. Biophys. 267, 690–700). By the above-described expression experiments in E. coli, it was confirmed that an active enzyme can be constructed by PFK-d alone. Assuming that the increase in the PFK activity observed in the tubers of line B75 is due to the expression of the introduced PFK-d gene, the result that the total PFK activity was increased is consistent with the result of the Western analysis.

A crude extract was prepared from a tuber (stored at 15° C. for 2 months after harvest), and PFK IV containing PFK-d was partially purified from the crude extract by using a Reactive Red 120 Agarose column (commercially available from Sigma) and a MonoQ column (commercially available from Pharmacia). The PFK activity of the partially purified PFK IV was measured at various low temperatures. The procedure of the above-described operation will now be described in detail. Firstly, a tuber having a weight of about 20 g of line B75 (stored at 15° C. for 2 months) was sliced to a thickness of about 2–5 mm and frozen in liquid nitrogen. The frozen slices were stored at −70° C. until use. All of the following operations were carried out at 4° C. In 40 ml of extraction buffer (the above-mentioned buffer A to which 2 mM benzamidine, 1 mM PMSF, 1 μM leupeptin, 1 μM pepstatin and 1% (w/v) insoluble polyvinylpyrrolidone were added), the frozen sample was sufficiently pulverized in a mortar using a pestle. The resulting extract was filtered through Miracloth and the filtrate was centrifuged at 20,000×g for 30 minutes. The supernatant was recovered and filtered (0.45 μm) and was applied to a Reactive Red 120 Agarose (Type 3000-CL, commercially available from Sigma) column (16×110 mm) to adsorb PFK. The procedure of purification from this point was the same as the above-described purification procedure of the PFK expressed in E. coli. By the MonoQ column chromatography, PFK was divided into 4 peaks and the fractions containing PFK IV were collected. The PFK activity was measured at various temperatures and Q10 values were determined. The results are shown in Table 9. The partially purified PFK IV was very stable at low temperatures, and the Q10 values were within the range between 1.9 and 2.0 at any temperature from 0°–25° C. The Q10 values of the PFKs purified from E. coli No. 58 strain are shown in Table 6. By comparing the results shown in Tables 6 and 9, it is seen that the PFK IV expressed in line B75 was more stable than the PFK expressed in E. coli, in spite of the fact that the same gene was introduced into both of them. Further, although the PFK gene introduced into line B75 was isolated from potato variety Brodick, it was more stable to cold temperature than PFK IV of the potato variety Brodick reported by Hammond et al (Hammond, J. B. W. et al., (1990) Planta., 180, 613–616). Based on the fact that ⅔ to ¾ of the PFK-d expressed in line B75 originated from the introduced gene judging from the Western analysis, and that PFK IV mainly contains PFK-d as reported by Kruger et al (Kruger, N. J. et al., (1989) Arch. Biochem. Biophys. 267, 690–700), it is thought that the cold stability of PFK IV of line B75 is brought about by the introduced gene.

Thus, the gene which was confirmed to express in E. coli was introduced into potato using the vector plasmid shown in FIG. 4. As a result, it was confirmed that the introduced gene was expressed in line B75 and that PFK IV of line B75 had cold stability.

TABLE 8

Total PFK Activity of Tubers of Line B75

| Line | PFK Activity (nmol/min/g, FW) |
|---|---|
| B40 (control) | 108.4 |
| B75 | 141.4 |

TABLE 9

Q10 Value of PFK IV Partially Purified from Tubers of Line B75

| Temperature (°C.) | 2 | 5 | 7 | 10 | 15 | 20 | 25 |
|---|---|---|---|---|---|---|---|
| Q10 Values | 1.91 | 1.92 | 1.92 | 1.93 | 1.94 | 1.95 | 1.96 |

18: Change in Sugar Content of Potato Tubers Stored at Low Temperature, to Which Cold Stable PFK Gene was Introduced, and Change in Color of Potato Chips Produced from the Tubers The sugar content of tubers of lines B75 and B40 stored at a low temperature (5°–8.5° C.), and the color of potato chips produced from the tubers were examined. The results are shown in Table 10. The glucose content was determined by using a commercially available test paper for measuring glucose in urine (Testape, commercially available from Shionogi & Co., Ltd.). More particularly, a spatula was inserted into a tuber to form a groove with a depth of about 5 mm. The test paper was inserted into this groove, and the glucose content was measured by comparing the color of the test paper with the color scale attached to the container of the test paper. The scores 0, +, ++, +++ and ++++ shown in the color scale attached to the container correspond to glucose concentrations of 0%, 0.1%, 0.25%, 0.5% and 2% or more, respectively. In Table 10, scores 0, +, ++, +++ and ++++ are expressed as values 0, 1.0, 2.0, 3.0 and 4.0, respectively. The values shown in Table 10 are averages of the measured values of 5 tubers. The smaller the value, the smaller the glucose content in the tuber. As shown in Table 10, it was confirmed that the glucose content in the tuber of line B75 stored at a low temperature for 4 weeks was smaller than that of line B40.

It is known that there is a strong correlation between the glucose content of a tuber and the color of the potato chips produced therefrom (Gray, D. and Hughes, J. C. (1978), The Potato Crop (ed. P. M. Harris), Chapman & Hall, London, pp.504–544). Thus, potato chips were produced from tubers of lines B75 and B40 stored at a low temperature (for 2 weeks, 4 weeks and 12 weeks) and the degree of browning was compared. More particularly, the tubers were sliced using a commercially available slicer and the slices were fried in an edible oil (mixture of rapeseed oil and soybean oil) at 180° C. for about 3 to 4 minutes until bubbles were no longer formed. Three potato chips from each of 5 tubers, totally 15 chips, per one line per one test were produced and the color of each potato chip was compared with color cards for potato chips (prepared by The Institute for Storage and Processing of Agricultural Produce, Wageningen, The Netherlands). The degree of browning is expressed in terms of the score described in the color card. The lower the score, the darker the fly color. The results are shown in Table 10. Each score is the average of 15 potato chips. The potato chips made from tubers of line B75 exhibited a lower degree of browning than those produced from line B40 irrespective of the duration of storage.

As described above, it was proved that the glucose content in the tubers stored at a low temperature can be decreased and, in turn, the degree of browning of potato chips can be decreased by transforming a potato plant using the vector plasmid shown in FIG. 4 and expressing the cold stable PFK in the tubers.

TABLE 10

Glucose Content in Tubers of Line B75 in Which Cold Stable PFK was Expressed and Color of Potato Chips Produced from the Tubers

| | Glucose Content (color score) Duration of Storage after Harvest (weeks) | | Potato Chip Color (color card score) Duration of Storage after Harvest (weeks) | | | |
|---|---|---|---|---|---|---|
| | 0 | 4 | 0 | 2 | 4 | 12 |
| B40 (control) | 1.0 | 2.6 | 7.0 | 4.0 | 2.6 | 2.3 |
| B75 | 1.0 | 1.2 | 7.0 | 5.5 | 3.7 | 3.5 |

We claim:

1. An isolated DNA molecule encoding plant ATP dependent fructose 6-phosphate 1-phosphotransferase.

2. The DNA according to claim 1, that encodes ATP dependent fructose 6-phosphate 1-phosphotransferase originating from a plant, wherein the Q10 value at 5° C. of the encoded enzyme is not more than 2.4.

3. The DNA according to claim 1, which encodes the amino acid sequence identified as SEQ ID NO: 2.

4. The DNA according to claim 3, which has the DNA sequence identified as SEQ ID NO: 1.

5. The DNA according to claim 1, which encodes the amino acid sequence identified as Sequence ID No. 4.

6. The DNA according to claim 5, which has the DNA sequence identified as Sequence ID No. 3.

7. The DNA according to claim 1, which encodes the amino acid sequence identified as Sequence ID No. 6.

8. The DNA according to claim 7, which has the DNA sequence identified as Sequence ID No. 5.

9. The DNA according to claim 1, which encodes the amino acid sequence identified as Sequence ID No. 8.

10. The DNA according to claim 9, which has the DNA sequence identified as Sequence ID No. 7.

11. The DNA according to claim 1, which encodes the amino acid sequence identified as Sequence ID No. 10.

12. The DNA according to claim 11, which has the DNA sequence identified as Sequence ID No. 9.

13. A recombinant vector comprising a DNA molecule encoding plant ATP dependent fructose 6-phosphate 1-phosphotransferase which can express said plant ATP dependent fructose 6-phosphate 1-phosphotransferase in a host cell.

14. A method for changing sugar content in plant cells under low temperature, which comprises transforming said plant with said recombinant vector according to claim 13.

15. The method according to claim 14, wherein said plant is potato.

16. The DNA of claim 1, which encodes plant ATP dependent fructose 6-phosphate 1-phosphotransferase derived from a plant selected from the group consisting of potato, Flaveria, rice, maize and radish.

17. The DNA of claim 1, which encodes a plant ATP dependent fructose 6-phosphate 1-phosphotransferase comprising the conserved amino acid sequences set forth in SEQ ID NOS: 11, 14, 21 and 22.

18. The DNA of claim 1, which encodes a plant ATP dependent fructose 6-phosphate 1-phosphotransferase comprising the conserved amino acid sequences set forth in SEQ ID NOS: 11–23.

19. The DNA of claim 16 or 17, wherein said DNA molecule is a genomic DNA molecule.

20. A recombinant vector which comprises DNA encoding plant ATP dependent fructose 6-phosphate 1-phosphotransferase comprising the conserved amino acid sequences set forth in SEQ ID NOS: 11, 14, 21 and 22.

21. A recombinant vector which comprises DNA encoding ATP dependent fructose 6-phosphate 1-phosphotransferase which has a Q10 value at 5° C. of not more than 2.4 and which comprises the conserved amino acid sequences set forth in SEQ ID Nos: 11–23.

22. The vector of claim 21, wherein said DNA encodes the polypeptide of SEQ ID NO:2.

23. The vector of claim 21, wherein said DNA molecule contains the DNA sequence set forth in the coding region of SEQ ID NO:1.

24. A cell which contains a recombinant DNA molecule encoding plant ATP dependent fructose 6-phosphate 1-phosphotransferase.

25. A cell which contains a recombinant DNA molecule encoding plant ATP dependent fructose 6-phosphate 1-phosphotransferase as defined in claim 16 or 17.

26. The cell of claim 24, wherein said DNA molecule contains genomic DNA encoding said ATP dependent fructose 6-phosphate dependent 1-phosphotransferase.

27. The cell of claim 24, which is a microorganism.

28. The cell of claim 24, which is a bacteria.

29. The cell of claim 24, which is a yeast.

30. The cell of claim 24, which is a plant cell.

31. The cell of claim 24, which is an animal or human cell.

32. A transformed plant which is transformed with the DNA molecule of claim 1, 16 or 17, wherein said plant expresses said DNA to produce said plant ATP dependent fructose 6-phosphate 1-phosphotransferase.

33. A transformed plant which is transformed with a DNA molecule encoding plant ATP dependent fructose 6-phosphate 1-phosphotransferase comprising the conserved amino acid sequences set forth in SEQ ID NOS: 11, 14, 21 and 22.

34. The transformed plant of claim 33, wherein said DNA encodes the polypeptide of SEQ ID NO:2.

35. The transformed plant of claim 33 or 34, which is a potato.

36. A method for making potato chips which comprises:

slicing a potato made by the method of claim 15 to prepare potato slices; and heating the potato slices to make potato chips.

37. The method of claim 36, wherein said potatoes are stored at a cold temperature at or below 15° C. before said potato chips are made.

* * * * *